United States Patent (10) Patent No.: US 7,678,374 B2
Anderson et al. (45) Date of Patent: Mar. 16, 2010

(54) VIRAL VECTORS EXPRESSING FUSION OF VIRAL LARGE ENVELOPE PROTEIN AND PROTEIN OF INTEREST

(75) Inventors: David Andrew Anderson, Brunswick (AU); Elizabeth Vera Ludmila Grgacic, Fitzroy North (AU)

(73) Assignee: Hepgenics Pty Ltd, Armadale, Victoria (AU)

( * ) Notice: Subject to any disclaimer, the term of this patent is extended or adjusted under 35 U.S.C. 154(b) by 81 days.

(21) Appl. No.: 10/553,683

(22) PCT Filed: Apr. 16, 2004

(86) PCT No.: PCT/AU2004/000511

§ 371 (c)(1),
(2), (4) Date: Oct. 18, 2006

(87) PCT Pub. No.: WO2004/092387

PCT Pub. Date: Oct. 28, 2004

(65) Prior Publication Data

US 2007/0099262 A1 May 3, 2007

(30) Foreign Application Priority Data

Apr. 17, 2003 (AU) .............................. 2003901876

(51) Int. Cl.
*A61K 39/00* (2006.01)
*C07K 14/00* (2006.01)
(52) U.S. Cl. .................................. 424/184.1; 530/350
(58) Field of Classification Search ........................ None
See application file for complete search history.

(56) References Cited

U.S. PATENT DOCUMENTS

2004/0001853 A1* 1/2004 George et al. ............ 424/189.1

FOREIGN PATENT DOCUMENTS

WO WO 02/10416 A1 2/2002

OTHER PUBLICATIONS

Glebe et al., Avian hepatitis B viruses: Molecular and cellular biology, phylogenesis, and host tropism, World J Gastroenterol, 2007, 13(1): 91-103.*
Ishikawa T. et al., "The Pre-S Domain of the Large Viral Envelope Protein Determines Host Range in Avian Hepatitis B Viruses", Proc. Natl. Acad. Sci. USA 92:6259-6263 (1995).
Kuroda S. et al., "Hepatitis B Virus Envelope L Protein Particles", The Journal of Biological Chemistry 267(3):1953-1961 (1992).
Netter H.J. et al., "Antigenicity and Immunogenicity of Novel Chimeric Hepatitis B Surface Antigen Particles with Exposed Hepatitis C Virus Epitopes", *Journal of Virology* 75(5):2130-2141 (2001), XP-002977998.
Bisht H. et al., "Recombinant Dengue Virus Type 2 Envelope/Hepatitis B Surface Antigen Hybrid Protein Expressed in *Pichia pastoris* Can Function as a Bivalent Immunogen", *Journal of Biotechnology* 99(2):97-100 (2002), XP-002425482.
Pumpens P. et al., "Evaluation of HBs, HBc, and frCP Virus-Like Particles for Expression of Human Papillomavirus 16 E7 Oncoprotein Epitopes", *Intervirology* 45(1):24-32 (2002), XP-008026494.
Firat H. et al., "Design of a Polyepitope Construct for the Induction of HLA-A0201-Restricted HIV 1-Specific CTL Responses Using *HLA-A* 0201 Transgenic, *H-2* Class I KO Mice", *European Journal of Immunology* 31(10):3064-3074 (2001), XP-002252815.
Hofmann C. et al., "Hepatocyte-Specific Binding of L/S-HBV Particles Expressed in Insect Cells", *Biological Chemistry* 376(3):173-178 (1995), XP-000910500.

* cited by examiner

*Primary Examiner*—Larry R Helms
*Assistant Examiner*—Nicole Kinsey White
(74) *Attorney, Agent, or Firm*—Scully, Scott, Murphy & Presser, P.C.

(57) ABSTRACT

The present invention provides a virus-like particle (VLP) comprising i) a polypeptide comprising a polypeptide of interest (POI) and at least a particle-associating portion of a large envelope (L) polypeptide of an avian hepadnavirus or a functional derivative or homolog thereof, and ii) a small envelope (S) polypeptide of an avian hepadnavirus or a functional derivative or homolog thereof. By introducing one or more POIs into the L polypeptide, the POI is translocated along with L into a particle structure made up primarily of S polypeptide. The present invention furthermore provides methods for producing a recombinant virus-like particle.

6 Claims, 12 Drawing Sheets

Figure 1:
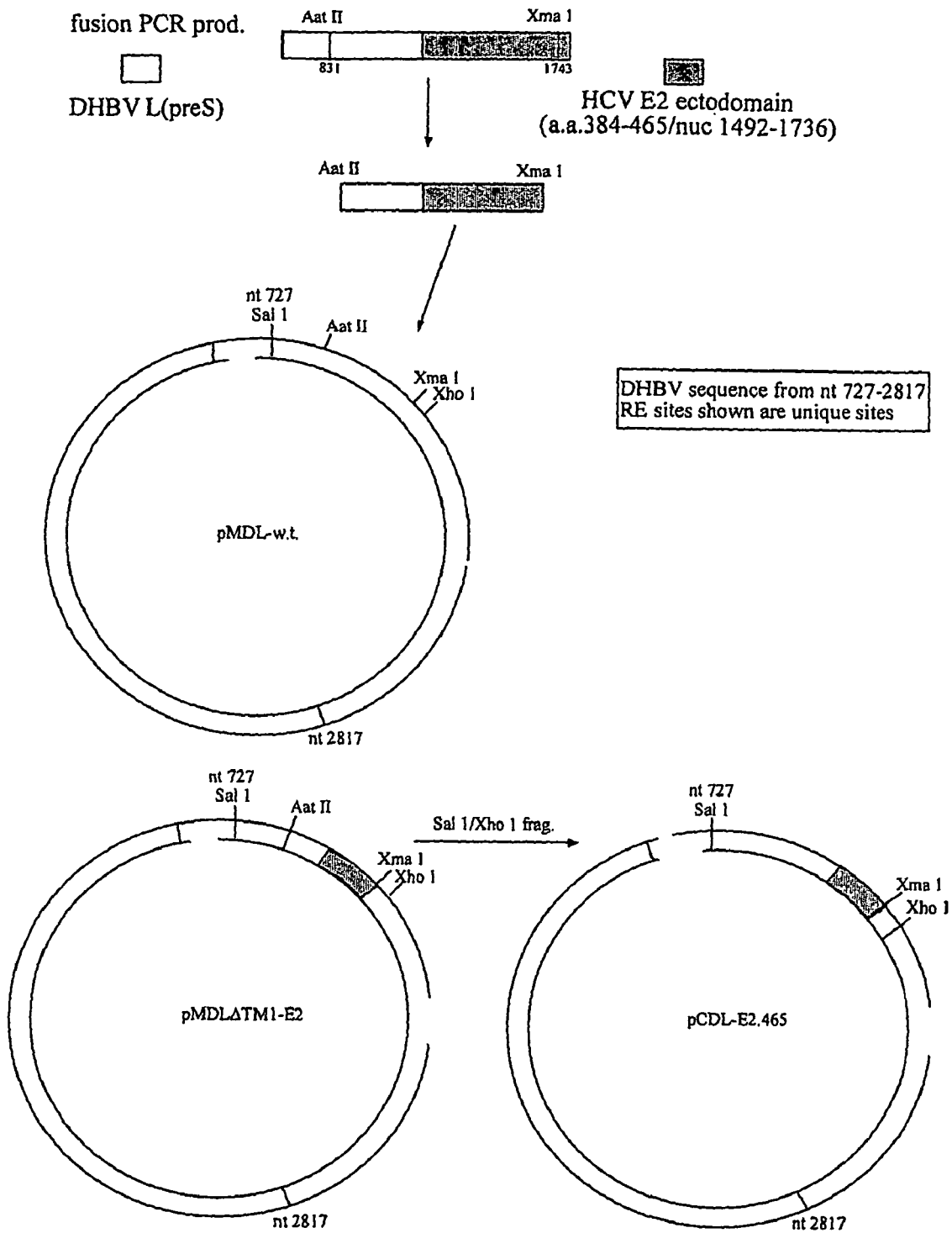
Figure 2:
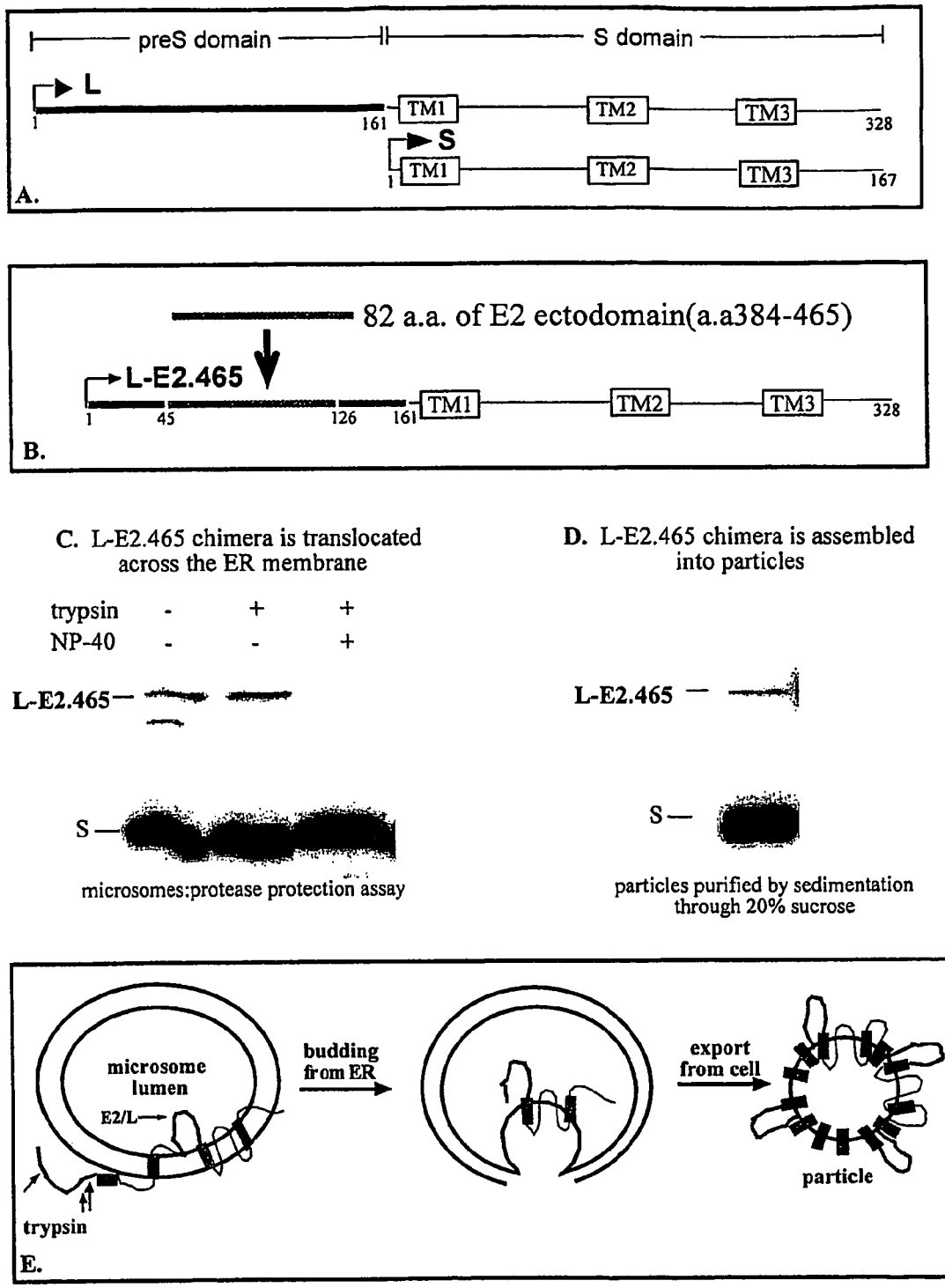

DHBV full genome sequence (US D16 Acc. No. K01839)

```
   1 catgctcatt tgaaagctta tgcaaaaatt aacgaggaat cactggatag ggctaggaga
  61 ttgctttggt ggcattacaa ctgtttactg tggggagaag ctcaagttac taactatatt
 121 tctcgtttgc gtacttggtt gtcaactcct gagaaatata gaggtagaga tgccccgacc
 181 attgaagcaa tcactagacc aatccaggtg gctcagggag gcagaaaaac aactacgggt
 241 actagaaaac ctcgtggact cgaacctaga agaagaaaag ttaaaaccac agttgtctat
 301 gggagaagac gttcaaagtc ccgggaaagg agagcccta cacccaacg tgcgggctcc
 361 cctctcccac gtagttcgag cagccaccat agatctccct cgcctaggaa ataaattacc
 421 tgctaggcat cacttaggta aattgtcagg actatatcaa atgaagggct gtacttttaa
 481 cccagaatgg aaagtaccag atatttcgga tactcatttt aatttagatg tagttaatga
 541 gtgcccttcc cgaaattgga aatatttgac tccagccaaa ttctggccca agagcatttc
 601 ctactttcct gtccaggtag gggttaaacc aaagtatcct gacaatgtga tgcaacatga
 661 atcaatagta ggtaaatatt taaccaggct ctatgaagca ggaatccttt ataagcggat
 721 atctaaacat ttggtcacat ttaaaggtca gccttataat tgggaacagc aacaccttgt
 781 caatcaacat cacatttatg atggggcaac atccagcaaa atcaatggac gtcagacgga
 841 tagaaggagg agaaatactg ttaaaccaac ttgccggaag gatgatccca aaagggactt
 901 tgacatggtc aggcaagttt ccaacactag atcacgtgtt agaccatgtg caaacaatgg
 961 aggagataaa caccctccag aatcagggag cttggcctgc tggggcggga aggagagtag
1021 gattatcaaa tccgactcct caagagattc ctcagcccca gtggactccc gaggaagacc
1081 aaaaagcacg cgaagctttt cgccgttatc aagaagaaag accaccggaa accaccacca
1141 ttcctccgtc ttcccctcct cagtggaagc tacaacccgg ggacgatcca ctcctgggaa
1201 atcagtctct cctcgagact catccgctat accagtcaga accagcggtg ccagtgataa
1261 aaactccccc cttgaagaag aaaatgtctg gtaccttcgg gggaatacta gctggcctaa
1321 tcggattact ggtaagcttt ttcttgttga taaaaattct agaaatactg aggaggctag
1381 attggtggtg gatttctctc agttctccaa agggaaaaat gcaatgcgct ttccaagata
1441 ctggagccca aatctctcca cattacgtag gatcttgccc gtggggatgc ccaggatttc
1501 tttggaccta tctcaggctt tttatcatct tcctcttaat cctgctagta gcagcaggct
1561 tgctgtatct gacggacaac gggtctacta tttaggaaa gctccaatgg gcgtcggtct
1621 cagccctttt ctcctccatc tcttcactac tgccctcgga tccgaaatct ctcgtcgctt
1681 taacgtttgg actttcactt atatggatga cttcctcctc tgccacccaa acgctcgtca
1741 ccttaacgca attagccacg ctgtctgctc tttttacaa gagttaggaa taagaataaa
1801 ctttgacaaa accacgcctt ctccggtgaa tgaaataaga ttcctcggtt accagattga
1861 tgaaaatttc atgaagattg aagaaagcag atggaaagaa ttaaggactg taatcaagaa
1921 aataaaagta ggagaatggt atgactggaa atgtattcaa agatttgtgg ggcatttgaa
1981 ttttgttttg cctttttacta aaggtaatat tgaaatgtta aaaccaatgt atgctgctat
2041 tactaaccaa gtaaacttta gcttctcttc atcctatagg actttgttat ataaactaac
2101 aatgggtgtg tgtaaattaa gaataaagcc aaagtcctct gtacctttgc cacgtgtagc
```

FIGURE 3

```
2161 tacagatgct accccaacac atggcgcaat atcccatatc accggcggga gcgcagtgtt
2221 tgcttttca aaggtcagag atatacatgt tcaggaacta ttgatgtctt gtttagccaa
2281 gataatgatt aaaccacgtt gtctcttatc tgattcaact tttgtttgcc ataagcgtta
2341 tcagacgtta ccatggcatt ttgctatgtt ggccaaacaa ttgctcaaac cgatacaatt
2401 gtactttgtc ccgagcaaat ataatcctgc tgacggccca tccaggcaca aacctcctga
2461 ttggacggct tttccataca cccctctctc gaaagcaata tatattccac ataggctatg
2521 tggaacttaa gaattacacc cctctccttc ggagctgctt gccaaggtat ctttacgtct
2581 acattgctgt tgtcgtgtgt gactgtacct ttggtatgta ccattgttta tgattcttgc
2641 ttatatatgg atatcaatgc ttctagagcc ttagccaatg tgtatgatct accagatgat
2701 ttctttccaa aaatagatga tcttgttaga gatgctaaag acgctttaga gccttattgg
2761 aaatcagatt caataaagaa acatgttttg attgcaactc actttgtgga tctcattgaa
2821 gacttctggc agactacaca gggcatgcat gaaatagccg aatcattaag agctgttata
2881 cctcccacta ctactcctgt tccaccgggt tatcttattc agcacgagga agctgaagag
2941 atacctttgg gagatttatt taaacaccaa gaagaaagga tagtaagttt ccaacccgac
3001 tatccgatta cggctagaat t
```

FIGURE 3 Cont.

DHBV L sequence (US D16) (start L atg 801; start S atg 1284)

```
801/1
atg ggg caa cat cca gca aaa tca atg gac gtc aga cgg ata gaa gga gaa ata ctg
 M   G   Q   H   P   A   K   S   M   D   V   R   R   I   E   G   E   I   L
861/21
tta aac caa ctt gcc gga agg atg atc cca aaa ggg act ttg aca tgg tca ggc aag ttt
 L   N   Q   L   A   G   R   M   I   P   K   G   T   L   T   W   S   G   K   F
921/41
cca aca cta gat cac gtg tta gac cat gtg caa aca atg gag gag ata aac acc ctc cag
 P   T   L   D   H   V   L   D   H   V   Q   T   M   E   E   I   N   T   L   Q
981/61
aat cag gga gct tgg cct ggg gcg gga agg aga gta gga tta tca aat ccg act cct
 N   Q   G   A   W   P   G   A   G   R   R   V   G   L   S   N   P   T   P
1041/81
caa gag att cct cag ccc cag tgg act ccc gag gaa gac caa aaa gca cgc gaa gct ttt
 Q   E   I   P   Q   P   Q   W   T   P   E   E   D   Q   K   A   R   E   A   F
1101/101
cgc cgt tat caa gaa aga cca ccg gaa gat ccc att cct ccg tct tcc cct cct
 R   R   Y   Q   E   R   P   P   E   D   P   I   P   P   S   S   P   P
1161/121
cag tgg aag cta caa ccc ggg gac gat cca ctc ctg gga aat cag tct ctc ctc gag act
 Q   W   K   L   Q   P   G   D   D   P   L   L   G   N   Q   S   L   L   E   T
1221/141
1251/151
```

FIGURE 4

```
cat ccg cta tac cag tca gaa cca gcg gtg ata aaa act ccc ccc ttg aag aag
 H   P   L   Y   Q   S   E   P   A   V   I   K   T   P   P   L   K   K
1281/161                                                          1311/171 aaa atg tct ggt acc ttc ggg gga ata cta gct ggc cta atc gga tta ctg gta agc ttt
 K   M   S   G   T   F   G   G   I   L   A   G   L   I   G   L   L   V   S   F
1341/181                                                          1371/191 ttc ttg ata aaa att cta gaa ata ctg agg agg cta gat tgg tgg att tct ctc
 F   L   I   K   I   L   E   I   L   R   R   L   D   W   W   I   S   L
1401/201                                                          1431/211 agt tct cca aag gga aaa atg caa tgc gct ttc caa gat act gga gcc caa atc tct cca
 S   S   P   K   G   K   M   Q   C   A   F   Q   D   T   G   A   Q   I   S   P
1461/221                                                          1491/231 cat tac gta gga tct tgc ccg tgg gga tgc cca gga ttt ctt tgg acc tat ctc agg ctt
 H   Y   V   G   S   C   P   W   G   C   P   G   F   L   W   T   Y   L   R   L
1521/241                                                          1551/251 ttt atc atc ttc ctc tta atc ctg cta gta tgg gca gca ggc ttg tca gcc ctt tcc atc
 F   I   I   F   L   L   I   L   L   V   W   A   A   G   L   S   A   L   F   I
1581/261                                                          1611/271 ggg tct act att tta gga aag ctc caa tgg gcg tcg gtc tca gcc ctt ttc tcc tcc atc
 G   S   T   I   L   G   K   L   Q   W   A   S   V   S   A   L   F   S   S   I
1641/281                                                          1671/291 tct tca cta ctg ccc tcg gat ccg aaa tct ctc gtc gct tta acg ttt gga ctt tca ctt
 S   S   L   L   P   S   D   P   K   S   L   V   A   L   T   F   G   L   S   L
1701/301                                                          1731/311
```

FIGURE 4 Cont.

```
1761/321
ata tgg atg act tcc tcc tct gcc acc caa acg ctc gtc acc tta acg caa tta gcc acg
 I   W   M   T   S   S   S   A   T   Q   T   L   V   T   L   T   Q   L   A   T
                                                    1791/331
ctg tct gct ctt ttt tac aag agt tag
 L   S   A   L   F   Y   K   S   *
```

FIGURE 4 Cont.

A. SigLΔTM1-E2.661 membrane fraction
B. LΔTM1-MSP2 membrane fraction
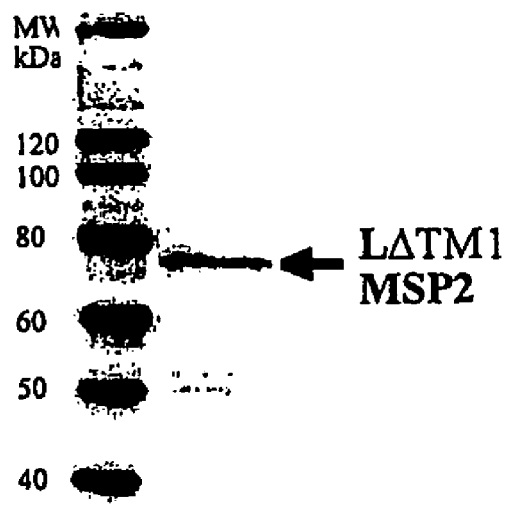
FIGURE 6

A. DL/S VLPs: sucrose step gradient profile
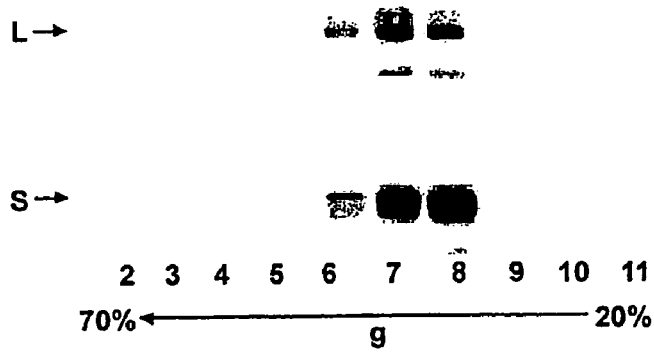
B. DLΔTM1-E2.465 VLPs: sucrose step gradient profile
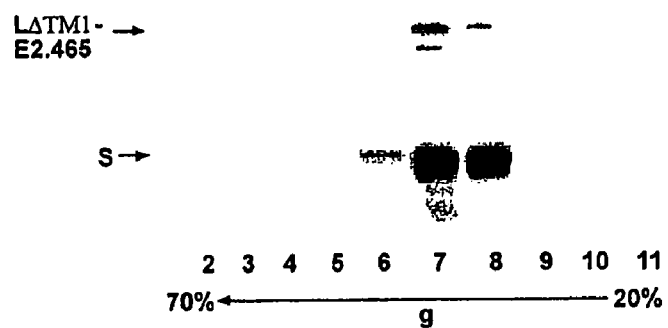
C. DLΔTM1-HpreS VLPs: sucrose step gradient profile
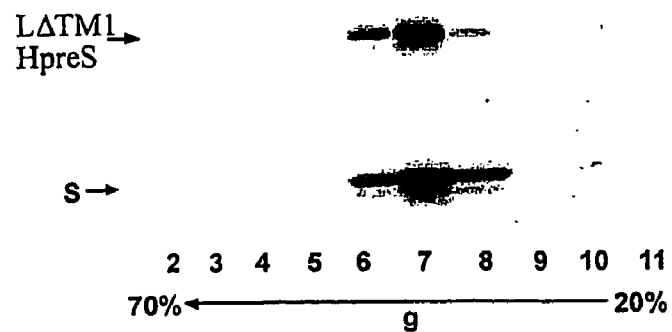
FIGURE 7

VIRAL VECTORS EXPRESSING FUSION OF VIRAL LARGE ENVELOPE PROTEIN AND PROTEIN OF INTEREST

BACKGROUND OF THE INVENTION

1. Field of the Invention

The present invention relates generally to virus-like particles (VLPs) for use in delivering a polypeptide of interest to a subject and to nucleic acid molecules encoding same. In particular, the present invention takes advantage of features of avian hepadnavirus particles to generate stable recombinant VLPs which are useful in the delivery to a subject of a polypeptide of interest. The polypeptide of interest may comprise one or more antigens capable of eliciting an immune response. The VLPs comprising the polypeptide of interest are useful for delivery of an antigen to the immune system of a subject or in the presentation of epitopes for the detection of antibodies in in vitro assays. The present invention extends, inter alia, to plasmids, cells, kits and methods which are useful in the generation, production, delivery and monitoring of the instant VLPs.

2. Description of the Prior Art

Bibliographic details of the publications referred to by author in this specification are collected at the end of the description.

Reference herein to prior art, including any one or more prior art documents, is not to be taken as an acknowledgment, or suggestion, that said prior art is part of the state of the art.

The hepadnaviruses are a family of enveloped DNA viruses. Assembly of mammalian hepadnaviruses, such as hepatitis B virus, is complex and mature virions are formed by the interaction of preformed cytoplasmic core particles with pre-assembled surface proteins on the host endoplasmic reticulum (ER) membrane. Following interaction with appropriate portions of envelope proteins, the nucleocapsids bud into the lumen of the ER along with a 1000-fold excess of empty, subviral particles (SVPs) and assembly is completed in an intermediate, pre-Golgi compartment (as reviewed by Nassal, M., *Curr. Top. Microbiol. Immunol.,* 214:297-337, 1996).

In many studies, virus-like particles (VLPs), which lack nucleocapsids, have proven to be promising candidate vaccines since they: (i) are non-infectious and therefore safe to produce and use, (ii) are more immunogenic than subunit vaccines because they provide the necessary spatial structure for display of epitopes, and (iii) elicit humoral, cell-mediated and importantly, mucosal immunity (Krueger, et al., *Biol. Chem.* 380:275-276, 1999).

A recent example of a successful VLP vaccine, currently in clinical trials, is the recombinant papillomavirus major capsid protein (L1) VLP, which prevents infection by inducing a strong neutralizing antibody response (Frazer, *Virus Research,* 89:271-274, 2002).

The hepatitis B virus (HBV) subviral particle (HBsAg-S) has been viewed as a candidate to produce recombinant VLPs. Several studies have examined which domains are suitable for insertion of foreign epitopes (Bruss et al., *EMBO J.,* 13:2273-2279, 1994., 1994; Delpeyroux et al, *J. Mol. Biol.* 195:343-350,1987), including N terminal fusion of the preS domain (Prange, et al, *J. Gen. Virol.* 76:2131-2140, 1995).

Most recently, particles carrying small, 35 amino acid insertions of the hepatitis C virus (HCV) hypervariable region 1 of the E2 envelope protein into the exposed 'a' determinant in the second hydrophilic loop have successfully elicited antibody responses (Netter, et al, *J. Virol.* 75:2130-2141, 2001).

Notably, there have been limitations to the size of the inserts tolerated for particle stability and a loss of immune reactivity to the 'a' determinant of HBsAg when particles were produced in a mammalian cell system (Prange et al, 1995, supra; Bruss et al, *J. Virol.* 65:3813-3820, 1991).

Particle instability with large fusions has recently been overcome with a Dengue virus/HBsAg fusion by expression in yeast (Bisht, et al, *J. Biotechnology.* 99:97-110, 2002).

However, in all these cases, in order to assemble chimeric particles, the recombinant S protein must assemble with wild type S subunits. These extended S chains present a difficulty for inclusion in the tight envelope lattice formed by the HBsAg (which excludes L) and so their number is limited, and consequently the immune response generated to the foreign epitopes is low.

Accordingly, there is a need for improved VLPs which efficiently incorporate polypeptides of interest.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Nucleotide and amino acid sequences are referred to by sequence identifier numbers (SEQ ID NO:). The SEQ ID NOs: correspond numerically to the sequence identifiers <400>1, <400>2, etc. A summary of sequence identifiers is provided in Table 1. A sequence listing is provided after the claims.

The envelope protein of duck hepatitis B virus (DHBV) and other avian hepadnaviruses consists of two proteins, the large envelope protein (L) and the small envelope protein (S), which are produced by differential in-frame translation initiation from a single preS/S open reading frame. L and S polypeptides have a common C terminal membrane spanning or S domain, while L has an approximately 160 amino acid N-terminal extension (or preS domain) encompassing a receptor binding region. The S polypeptide is the major viral envelope constituent, which determines envelope curvature and can drive particle secretion even in the absence of the nucleocapsid. In contrast L polypeptide can only be exported when co-assembled with S.

The assembly of DHBV envelope proteins and their involvement in host cell entry are closely linked to a unique topological switch adopted by hepadnaviruses, in which a large N-terminal preS domain of the L protein is post-translocationally translocated across the ER membrane. This process is regulated so that generally only approximately 50% of molecules have translocated N-termini and the mature particle contains mixed internal/external topologies, including a partially translocated or intermediate form.

The present invention is predicted, in part, on the surprising discovery that substantial regions of L polypeptide of DHBV are dispensable for L translocation and particle assembly, including regions in the S domain which have the same amino acid sequence as S polypeptide regions essential for particle assembly. Accordingly, L polypeptides are more flexible in their particle association than S polypeptides and thus open to more extensive manipulation.

The present invention, therefore, provides virus-like particles (VLPs) which primarily contain a small envelope (S) polypeptide or a functional derivative or homolog thereof. In addition, and in accordance with the present invention however, they comprise a fusion polypeptide comprising a polypeptide of interest (POI) and at least a particle associating portion of a large envelope (L) polypeptide or a functional derivative or homolog thereof. Because the L polypeptide is not excluded during VLP assembly and because it can be extensively manipulated to vector a heterologous polypeptide without significantly affecting particle stability, the VLP of the present invention will be useful, inter alia, in the delivery of a polypeptide of interest to a subject. In addition, because epitopes of an antigenic POI will be effectively displayed in a VLP, the VLPs are useful in assays for the detection of antibodies.

The present invention is described with particular reference to DHBV, however, the invention extends to L and S polypeptides from other viruses with L and S envelope polypeptides proteins in which L is not excluded from particle assembly. For example, L and S polypeptides from other avian hepadnaviruses are contemplated such as, but not limited to such heron (HHBV), snow goose (SGHBV) and hepadnaviruses which exhibit similar subviral particle morphology to DHBV, i.e., with L and S envelope proteins. The S domains of L and S polypeptides are highly conserved within all hepadnaviruses, exhibiting for example up to 70% amino acid similarity in the region between TM1 and TM2.

The present invention provides a virus-like particle (VLP) comprising i) a polypeptide comprising a polypeptide of interest (POI) and at least a particle associating portion of a large envelope (L) polypeptide of an avian hepadnavirus or a functional derivative or homolog thereof, and ii) a small envelope (S) polypeptide of an avian hepadnavirus or a functional derivative or homolog thereof.

The present invention furthermore provides, a virus-like particle (VLP) comprising i) a fusion polypeptide comprising a polypeptide of interest (POI) and at least a particle associating portion of a large envelope (L) polypeptide of DHBV or a functional derivative or homolog thereof, and ii) a small envelope (S) polypeptide of DHBV or a functional derivative or homolog thereof.

By introducing one or more POIs into the L polypeptide, the POI is translocated along with L into a particle structure made up primarily of S polypeptide.

Although several examples of particle associating portions of the L polypeptide are provided, based on the teaching provided herein it would be well within the skill of the addressee to generate smaller or larger portions of L-polypeptide and determine whether they, together with a heterologous (or indigenous) protein of interest, are capable of particle association within a VLP. Accordingly, the present invention is in no way limited to the exemplified constructs.

The virus-like particles of the present invention are useful in vaccine compositions to promote an effective immune response. In particular embodiments, the virus-like particles are advantageously a suitable size to be taken up by antigen presenting cells, such as dendritic cells. For example, DHBV VLPs are significantly larger than mammalian HBV VLPs.

Recombinant VLPs of the present invention are prepared using expression plasmids comprising nucleic acid molecules encoding the recombinant L polypeptides separately or together with S polypeptides. Expression plasmids are conveniently in a form suitable for expression in yeast, baculovirus or avian or mammalian expression systems. Plasmids comprising nucleic acid molecules encoding the instant recombinant L polypeptides may also be used to deliver nucleic acid constructs directly to the cells of a subject.

Alternatively, kits are contemplated to facilitate recombinant production of the instant fusion proteins.

The present invention furthermore provides methods for producing a recombinant virus-like particle and compositions comprising a virus-like particle derived from L and S polypeptide of avian hepadnaviruses or other non-L excluding viruses for use as a vaccine or source of antigen wherein the L polypeptide comprises one or more antigens of interest derived from one or more heterologous sources.

BRIEF DESCRIPTION OF THE DRAWINGS

FIG. 1 is a schematic representation of a cloning strategy for generating $_p$CDL-E2.465

FIG. 2A is a schematic representation of the large (L) and small (S) envelope proteins of DHBV. L and S are produced by differential translation from a single open reading frame such that L protein consists of a preS domain of 161 amino acids and a C-terminal S domain of 167 amino acids, which comprises the S protein. The three transmembrane domains (TM) are indicated by the boxes.

FIG. 2B is a schematic representation of L showing where the 82 amino acid portion of the HCV E2 ectodomain (from aa 384 to 465) was inserted into the preS domain, generating the E2.465/L chimeric envelope protein.

FIG. 2C provides the results of a Western Blot showing that the E2.465/L chimera is translocated across the ER. Protease protection analysis of ER microsomes prepared from LMH cells transfected with pCDL-E2.465 and pCI-S (an S protein expression plasmid). Microsomes samples were subjected to digestion with trypsin in the absence or presence of the detergent, NP-40, or left untreated, as denoted above each lane. Protease protection of E2.465/L chains was analysed by SDS-PAGE and Western blotting with a monoclonal anti-S antibody, which detects both E2.465/L and S proteins. Protection of E2.465/L from trypsin digestion (middle lane) is an indication of translocation to the ER lumen.

FIG. 2D provides the results of a Western Blot showing that the E2.465/L chimera is assembled into particles. Intracellular particles were isolated from avian hepatoma (LMH) cells transfected with pCDL-E2.465 and pCI-S by freeze-thawing cells 3 times, centrifugation to obtain the cytosolic fraction for sedimentation of particles through 20% sucrose on to a 70% sucrose cushion at 38,000 r.p.m. (SW41 rotor Beckman). The particle fraction at the 20-70% sucrose interface was methanol precipitated prior to SDS-PAGE and analysis of envelope proteins by Western blotting.

FIG. 2E is a schematic representation modelling the membrane orientations of L protein on the ER (depicted as microsome vesicles), showing the process of post-translational translocation to the microsome lumen, which confers protection from trypsin digestion of the E2.465/L hybrid chains. During particle assembly assembled envelope proteins bud from the ER into the ER lumen taking the inner leaflet of the ER membrane. Particles are exported from the cell via the cellular vesicular export pathway enabling isolation of particles both from the cytosolic (as shown in D) and extracellular compartments. Envelope protein domains translocated to the ER lumen are thus ultimately exposed to the outside of the assembled particle, as indicated by the schematic diagram of a particle.

FIG. 3 is a representation showing the genomic nucleotide sequence of DHBV (SEQ ID NO: 5).

FIG. 4 is a representation showing provides the amino acid sequences of the L (SEQ ID NO: 7) and the S (SEQ ID NO: 13) polypeptides of DHBV. Start sites are underlined and stop sites are starred (*).

FIG. 5A is a schematic representation of DHBV L and DHBV S protein.

FIG. 5B to 5H is a schematic representation of DHBV L chimeras. Boxes labelled TM1-3 represent the transmembrane domains. Numbers along the length of the DHBV L represent amino acid positions relative to the DHBV L sequence. The ∇ indicates a deletion in TM1.

FIGS. 6A and 6B is a schematic representation showing results of Western blots of a membrane fraction of LMH cells transfected with pSigLΔTM1-E2.661 (A) or pCDLΔTM1-MSP2 (B). MW markers (40-120 kDa) are included to indicate the size of the chimeric L proteins.

FIGS. 7A and 7B is a schematic representation showing a Western blot of fractions from a sucrose step gradient showing that Dl/S (A) and chimeric L VLPs, DLΔTM1-E2.465/S (B) and DLΔTM1-HpreS (C) produced in yeast have the same particle density. VLPs produced in yeast sedimented through 20% sucrose on to a 70% cushion were further sedimented on a 20-70% sucrose step gradient for 5 hours at 38,000 rpm. Fractions collected from the gradient (no.s 2-11) were run on an SDS-PAGE and Western blotted with a monoclonal against the DHBV S domain.

Figure 8:
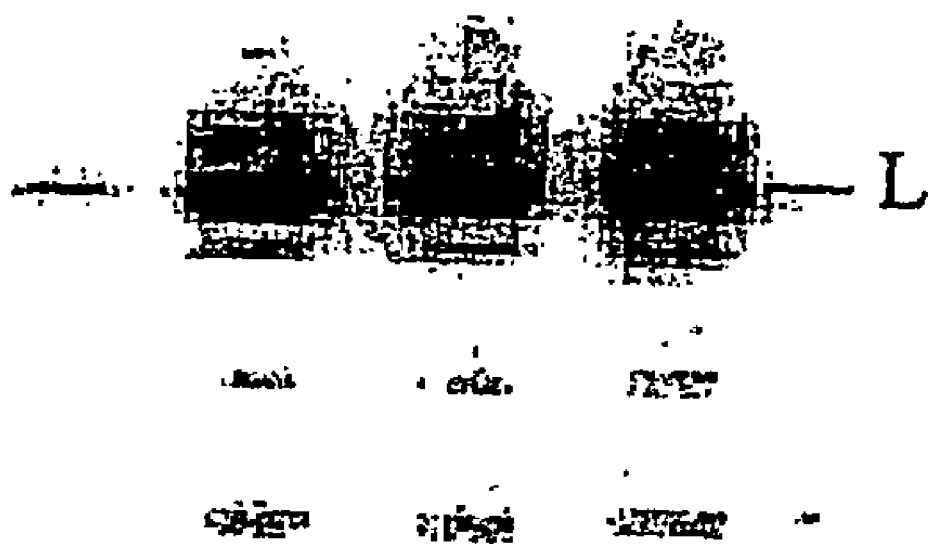

FIG. 8 is a schematic representation showing a Western blot of DHBV L protein probed with the sequential bleeds of one rat immunised with DL/S VLPs produced in yeast. Pre refers to the bleed taken before immunisation and nos 1-5 represent rat sera obtained at 3,6,9 and 13 weeks.

TABLE 1

| SEQ ID NO. | SEQUENCE |
| --- | --- |
| SEQ ID NO: 1 | Primers for generating L-fusion proteins |
| SEQ ID NO: 2 | Primers for generating L-fusion proteins |
| SEQ ID NO: 3 | Primers for generating L-fusion proteins |
| SEQ ID NO: 4 | Primers for generating L-fusion proteins |
| SEQ ID NO: 5 | Full genomic nucleotide sequence of DHBV |
| SEQ ID NO: 6 | Nucleotide sequence encoding L polypeptide of DHBV |
| SEQ ID NO: 7 | Amino acid sequence of L polypeptide of DHBV |
| SEQ ID NO: 8 | Nucleotide sequence encoding S domain of L polypeptide of DHBV |
| SEQ ID NO: 9 | Amino acid sequence of S domain of L polypeptide of DHBV |
| SEQ ID NO: 10 | Nucleotide sequence encoding preS domain of L polypeptide of DHBV |
| SEQ ID NO: 11 | Amino acid sequence of pre S domain of L polypeptide of DHBV |
| SEQ ID NO: 12 | Nucleotide sequence encoding S polypeptide of DHBV |
| SEQ ID NO: 13 | Amino acid sequence of S polypeptide of DHBV |

DETAILED DESCRIPTION OF THE INVENTION

The present invention is predicated in part on the finding that L polypeptide of DHBV can be substantially modified yet still retain the ability to associate with S polypeptides of DHBV during virus-like particle assembly.

It is proposed herein to use an L polypeptide or a functional derivative or homolog thereof to deliver a polypeptide or peptide of interest to a subject. In particular, it is proposed to use an L polypeptide to deliver antigens of interest to the immune system of a subject as part of a virus-like particle.

In a broad embodiment the present invention provides a virus-like particle (VLP) comprising a fusion (chimeric) polypeptide comprising a polypeptide of interest (POI) and a particle associating portion of a large envelope (L) polypeptide.

The virus-like particle is primarily composed of a small envelope (S) polypeptide.

Accordingly, the present invention furthermore provides a VLP comprising i) fusion polypeptide comprising a polypeptide of interest (POI) and at least a particle associating portion of a large envelope (L) polypeptide or a functional derivative or homolog thereof, and ii) a small envelope (S) polypeptide of an avian hepadnavirus or a functional derivative or homolog thereof.

More specifically, the present invention furthermore provides a VLP comprising i) a fusion polypeptide comprising a polypeptide of interest (POI) and at least a particle associating portion of a large envelope (L) polypeptide of DHBV or a functional derivative or homolog thereof, and ii) a small envelope (S) polypeptide of DHBV or a functional derivative or homolog thereof.

Preferably at least part of said POI is exposed on the surface of the virus-like particle.

The term "virus-like particle" is used in its broadest sense to mean a particle or three dimensional proteinaceous structure which, like sub-viral particles of enveloped viruses, form particles by self-assembly or folding of envelope polypeptides within a lipid bilayer. The virus-like particles of the present invention may be recombinant or synthetic or may comprise a combination of synthetic and recombinant components.

Reference herein to the singular form such as "a", "an" or "the" includes the plural aspect unless the context clearly specifies otherwise. Thus, reference for example to "a polypeptide of interest" includes a single polypeptide, as well as two or more such polypeptides.

Reference herein to the term "polypeptide" means a polymer of amino acids and should not be limited to any particular length. Therefore, the term includes proteins, oligopeptides, peptides and epitopes. The term does not exclude modifications of the polypeptide, for example myristylation, glycosylation, phosphorylation, addition of N-terminal signal sequences and the like. Included within the definition are, for example, polypeptides containing one or more analogs of an amino acid (including for example, unnatural amino acids such as those give in Table 2) or polypeptides with substituted linkages.

Analogs contemplated herein include but are not limited to modification to side chains, incorporating of unnatural amino acids and/or their derivatives during peptide, polypeptide or protein synthesis and the use of crosslinkers and other methods which impose conformational constraints on the proteinaceous molecule or their analogs.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitization, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH, palmitylation of cysteine residues.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid, contemplated herein is shown in Table 2.

TABLE 2

Codes for non-conventional amino acids

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-Nmethylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylethyl)glycine | Nhtrp |

TABLE 2-continued

Codes for non-conventional amino acids

| Non-conventional amino acid | Code | Non-conventional amino acid | Code |
|---|---|---|---|
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | | |

Crosslinkers can be used, for example, to stabilize 3D conformations, using homo-bifunctional crosslinkers such as the bifunctional imido esters having $(CH_2)_n$ spacer groups. with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids and the introduction of double bonds between $C_\alpha$ and $C_\beta$ atoms of amino acids.

The terms "fusion polypeptide" or "chimeric polypeptide" or "hybrid polypeptide" are interchangably used to mean a polypeptide, protein or peptide comprising two or more associated polypeptides which are expressed as part of the same expression product, or which are generated by synthetic means. Fusion polypeptides may comprise two or more L and POI polypeptides and intervening regions such as, for example, linker or spacer regions. In particular, regions which permit or directly or indirectly facilitate a surface topology or increase protease resistance for the polypeptide of interest in the particle are contemplated, for example, N-terminal signal sequences. An example of a signal sequence is preprolactin however there are many other suitable signal sequences, as will be understood by one of skill in the art. An example of a spacer region is a transmembrane domain. Alternatively, or in addition, regions which promote a cytosolic topology may be included. Polypeptide topology in a viral particle may be assessed for example by protease protection assay or by determining interactivity with antibodies determined by the L polypeptide, S polypeptide, the polypeptide of interest or epitopes generated through fusion of these polypeptides. According, the term "fusion" in "fusion polypeptide" is not used in the sense of "viral fusion".

The term "polypeptide of interest" means any polypeptide which is advantageously delivered to a subject as part of a virus-like particle. For example, two or more or a matrix of polypeptides involved in promoting and/or mediating a particular biochemical or physiological reaction may be delivered to a subject in viral particle form. A particular reaction contemplated is an immune response to an antigen. Accordingly the term includes any antigenic polypeptide of interest. Antigenic polypeptides may be co-expressed with immunopotentiating polypeptides such as cytokines as is well known in the art. The polypeptides and peptides of the present invention (POIs) may furthermore be expressed or synthesised in L with molecules which serve as targeting and/or marker molecules such as, without limitation, molecules which assist in targeting and/or marking particular cells, such as dendritic or other antigen presenting cells.

"Subject" as used herein refers to an animal, preferably a mammal and more preferably human who can benefit from administration of the viral particles of the present invention. There is no limitation on the type of animal that could benefit from the presently described molecules. A patient regardless of whether a human or non-human animal may be referred to as an individual, subject, animal, host or recipient. The molecules and methods of the present invention have applications in human medicine, veterinary medicine as well as in general, domestic or wild animal husbandry. For convenience, an "animal" includes an avian species such as a poultry bird, an aviary bird or game bird.

The preferred animals are humans or other primates, livestock animals, laboratory test animals, companion animals or captive wild animals.

Examples of laboratory test animals include ducks, snow geese, mice, rats, rabbits, guinea pigs and hamsters. Rabbits and rodent animals, such as rats and mice, provide a convenient test system or animal model. Livestock animals include sheep, cows, pigs, goats, horses and donkeys. Non-mammalian animals such as avian species, zebrafish and amphibians are also contemplated.

The terms "antigen" or "antigenic polypeptide" are used in their broadest sense to include polypeptides which are capable of inducing an immune response in a subject. The antigenic polypeptide may comprise single epitope regions through to multiple epitope regions including repeated epitope regions. The antigenic polypeptide may derive from a single or multiple sources although antigens from infectious agents, such as, for example, viruses, bacteria, fungi, protozoa, trematodes, nematodes, prions and the like are contemplated, as are tumour-related antigens. Antigenic regions of many agents and tumour-related proteins are well known in the art. Antigens are, for example, those from parasites, bacteria, viruses, cancers and those described herein include antigens from E2 polypeptide of Hepatitis, MSP2 polypeptide from *P. falciparum* and H protein from measles.

As is well know to those skilled in the art, effective immune responses for prophylactic or therapeutic vaccines generally elicit strong CTL and T-helper cell responses as well as strong humoral responses.

The antigenic polypeptide of interest may comprise epitope regions from two or more polypeptides from different organisms, species or subspecies. For example, viral and bacterial or multiple viral or multiple bacterial infectious may be vaccinated for simultaneously.

The phrase "particle associating portion" means for all L polypeptides, that or those portions of the L polypeptide which is/are required for L polypeptide incorporation into virus-like particles. For example, the TM1 region of the S domain of L is not required for L association with the particle and may be omitted from the L-polypeptide used herein. Indeed, as contemplated herein, the sequences downstream of TM1 (or downstream of TM2 and the 5' cysteine loop) of L polypeptide are sufficient for particle association. Similarly, the preS domain of L is not required for assembly of L in the particles. The S domain of L absent TM1 is an example of a particle associating portion of L. Many different particle association portions are clearly available pursuant to the present invention. The nature of this portion is flexible and may be determined empirically using methods known in the art and referred to herein.

Although a minimum functional portion of L may be advantageous in some applications, the present invention extends full length L polypeptides interspersed with a POI or wherein the POI is terminally appended. Preferably the POI is introduced into surface exposed portions of L.

The term "derived from" means that a particular element or group of elements has originated from the source described, but has not necessarily been obtained directly from the specified source.

The term "isolated" includes reference to VLPs having undergone at least one purification step, conveniently described in terms of the % of pure material in a sample. Preferred forms include material which is at least 50% pure, more preferably at least 60%, more preferably at least 70%, more preferably at least about 80%, still more preferably at least about 90% pure VLP material in a sample.

One of the advantages of the present invention is that VLPs may be produced of generally consistent size.

In another aspect of the present invention an isolated virus-like particle (VLP) is contemplated comprising i) a fusion polypeptide comprising a polypeptide of interest (POI) and at least a portion of the S domain of a large envelope (L) polypeptide of an avian hepadnavirus such as DHBV or a functional derivative or homolog thereof; and ii) a small envelope (S) polypeptide of an avian hepadnavirus such as DHBV or a functional derivative or homolog thereof, wherein at least a part of said POI is exposed on the surface of the virus-like particle.

Signal sequences may conveniently be employed in order to effect expression of particular POI/L polypeptides in some expression systems, as required. As described herein, the presence of a strong signal sequence is also used to enhance the amount of POI expressed on the surface of the VLP.

Exemplary portions of L are amino acids 24 to 167 of DHBV S domain or, more preferably at least TM2 (including the 5' cysteine loop between TM1 and TM2) and downstream sequences of L polypeptide of DHBV.

In one particular embodiment of the present invention, the polypeptide of interest is located at the amino terminal side of the S domain amino acid sequence of the L polypeptide or the S domain minus the TM1 domain. In another embodiment, the POI is located in the pre-S domain of the L polypeptide or N terminally to the L polypeptide.

By introducing one or more POIs into the pre-S domain of L or N terminally to the S domain of L or N-terminally to the S domain absent TM1, the POI is translocated along with L into a particle structure made up primarily of S polypeptide. This facilitates a high copy number of POI per VLP.

In one embodiment the virus-like particles of the present invention are useful in vaccine compositions to promote an effective immune response. In particular, the virus like particles are advantageously a suitable size to be taken up by antigen presenting cells, such as dendritic cells. Specifically, in relation to mammalian hepadnavirus particles, these are typically approximately 20 nanometers, while those of avian hepadnaviruses are pleomorphic and are typically between 35 and 60 nanometers in diameter. An effective immune response is one which is capable of reducing the number of target antigens in a subject and may prevent infections or development of disease conditions (prophylactic vaccine) or may treat current infections or conditions (therapeutic vaccination).

Without being bound to any particular theory, the VLPs of the present invention are capable of stimulating humoral and/or cell mediated immune responses. Heterologous antigens are targeted to appropriate pathways of MHC class 1 and class 11 antigen processing and presentation, and are targeted for dendritic cells which initiate, in particular T-cell responses.

In another aspect, preferred L polypeptides comprise or consist of an amino acid sequence substantially set forth in SEQ ID NO: 7 and SEQ ID NO: 9, or an amino acid sequence having at least 50% similarity to SEQ ID NO: 7 or SEQ ID NO: 9.

Even more preferably, the % similarity exceeds 60% identity, more preferably 70% identity, still more preferably at least about 80%, still more preferably about 90-95% identity.

Preferred L polypeptides are derived from an avian hepadnavirus such as but not limited to DHBV. Importantly, the hepadnavirus or the envelope polypeptides employed in the present invention do not exclude L from VLP assembly.

Functional derivatives of the instant L polypeptide include fragments, parts or portions of the parent molecule which retain the ability of the L polypeptide to associate with the particle formed by S polypeptide, or at least where such ability is not substantially lost.

Functional derivatives of the instant S polypeptide retain the ability of the ability of the S polypeptide to form virus-like particles, or at least where such ability is not substantially lost.

Substantial loss would mean that the L particle is assembled with S in particles at a ratio of less than about 1:1 or more preferably less than about 1:2, even more preferably less than about 1:3, still even more preferably less than about 1:4.

A preferred S polypeptide is derived from an avian hepadnavirus such as but not limited to DHBV or comprises or consists of an amino acid sequence substantially set forth in SEQ ID NO: 13.

The term "functional derivative" also extends to polypeptides having one or more amino acid mutations or modifications. Mutations may be derived from additions, insertions, deletions or substitutions of amino acids. Substitutions are preferably conservative amino acid substitutions within the following groups: glycine and alanine; valine, isoleucine and leucine; aspartic acid and glutamic acid; asparagine and glutamine; serine and threonine; lysine and arginine; and phenyl alanine and tyrosine. Modifications may include the addition of flanking sequences which enhance viral particle assembly or stability.

Preferably, derivatives have at least 60% amino acid similarity, or more preferably at least 80%, or most preferably 90% or greater similarity to all or part of the parent molecules.

Accordingly, in another embodiment, the present invention provides a VLP comprising a fusion polypeptide comprising a POI and a particle associating portion of an L polypeptide wherein said L polypeptide comprises a sequence of amino acids substantially as set forth in SEQ ID NO: 7 or SEQ ID NO: 9 or an amino acid sequence having at least about 50% similarity thereto, or a functional derivative or homolog thereof In another embodiment, the present invention provides a VLP comprising a fusion polypeptide comprising a POI and a particle associating portion of an L polypeptide wherein said L polypeptide is encoded by a sequence of nucleotides substantially as set forth in SEQ ID NO: 6 or SEQ ID NO: 8 or a sequence of nucleotides capable of hybridizing to SEQ ID NO: 6 or SEQ ID NO: 8, or a complementary form thereof under medium stringency conditions.

The VLPs of the present invention are assembled in vitro or in vivo using techniques which are well known to those of ordinary skill in the art such as those described or referred to herein or summarised in Sambrook et al. Specifically expression plasmids designed to express one or more recombinant envelope proteins as described herein are generated.

Accordingly, in another aspect, the present invention provides an isolated or recombinant polypeptide for use in the assembly of a VLP comprising a polypeptide of interest (POI) and at least a particle-associating portion of a large envelope polypeptide (L) of an avian hepadnavirus such as DHBV or a functional derivative or homolog thereof.

In a related aspect, the present invention provides a recombinant polypeptide capable of assembling into a VLP when expressed in a cell, said polypeptide comprising a polypeptide of interest (POI) and at least a particle-associating portion of a large envelope polypeptide (L) of an avian hepadnavirus such as DHBV or a functional derivative of homolog thereof.

Preferably, the particle-associating portion of L comprises at least the S domain of L or the S domain of L minus the TM1 domain or a functional derivative thereof.

Still more preferably, the POI is located in the pre-S domain of L or at the amino terminal side of the S domain of L, or the S domain minus the TM1 domain of L.

In accordance with this aspect of the present invention, the L polypeptide comprises an amino acid sequence substantially as set forth in SEQ ID NO: 7 or SEQ ID NO: 9 or comprises an amino acid sequence having at least 50% similarity to SEQ ID NO: 7 or SEQ ID NO: 9.

As described herein, the particle-associating portion of L polypeptide consists of an amino acid sequence substantially as set forth in SEQ ID NO: 7 or SEQ ID NO: 9 or a functional derivative thereof comprising an amino acid sequence having at least 50% similarity to SEQ ID NO: 7 or SEQ ID NO: 9.

Avian hepadnaviruses exhibit considerable sequence identity and accordingly, sequences having greater than 70% similarity or identity are contemplated.

The present invention extends to the use in the manufacture of a VLP of an L polypeptide or particle associating portion thereof is encoded by a sequence of nucleotides substantially as set forth in SEQ ID NO: 6 or SEQ ID NO: 8 or having at least about 50% similarity to SEQ ID NO: 6 or SEQ ID NO: 8 or a contiguous sequence of nucleotides capable of hybridizing to a complementary form SEQ ID NO: 6 or SEQ ID NO: 8 under hybridisation conditions of medium stringency.

In a further aspect of the invention, the L polypeptide further comprises a signal sequence. Such sequences are particularly useful in enhancing surface expression of a POI in the VLP.

Preferred L polypeptides are DHBV L polypeptide or functional derivative thereof.

In yet another aspect, the present invention provides a nucleic acid molecule comprising a sequence of nucleotides encoding a fusion polypeptide suitable for use in making a recombinant VLP, wherein said nucleic acid molecule encodes a POI and a particle associating portion of an L polypeptide and wherein the sequence of nucleotides encoding the particle associating portion of an L polypeptide comprises the sequence set forth in SEQ ID NO: 6 or SEQ ID NO: 8 or a contiguous sequence of nucleotides capable of hybridizing thereto or to a complementary form thereof under low stringency hybridisation conditions, or a functional derivative or homolog thereof.

In yet still another aspect, the present invention provides a nucleic acid molecule comprising a sequence of nucleotides encoding a fusion polypeptide suitable for use in making a recombinant VLP, wherein said nucleic acid molecule encodes a POI and a particle associating portion of an L polypeptide and wherein the nucleic acid encoding the particle associating portion of an L polypeptide encodes the amino acid sequence set forth in SEQ ID NO: 7 or SEQ ID NO: 9 or an amino acid sequence having at least about 50% similarity thereto, or a functional derivative or homolog thereof.

In another aspect, the present invention provides a nucleic acid molecule comprising a sequence of nucleotides encoding a fusion polypeptide suitable for use in making a recombinant VLP, wherein said nucleic acid molecule encodes a POI and a particle associating portion of an L polypeptide and wherein the nucleic acid encoding the particle associating portion of an L polypeptide encodes the amino acid sequence set forth in SEQ ID NO: 7 or SEQ ID NO: 9

Yet another aspect of the present invention provides a recombinant nucleic acid molecule for use in making a recombinant VLP, said nucleic acid molecule comprising a sequence of nucleotides encoding at least a particle-associating portion of an L polypeptide of an avian hepadnavirus such as DHBV or a functional derivative or homolog thereof comprising one or more cloning sites suitable for accepting a second nucleic acid molecule encoding one or more polypeptide of interest, wherein said polypeptides of interest is expressed as a fusion polypeptide with said L polypeptide. The expression vectors of the present invention may also conveniently express other envelope proteins such as L or, preferably, S polypeptide. Thus bidirectional or bicistronic promoters may routinely be employed in order to express recombinant L and also S polypeptide from the same vector. In addition, signal sequences are employed to enhance expression including surface expression, of the POI. Cells and kits comprising the instant recombinant nucleic acid molecules are expressly encompassed.

The present invention therefore provides a method of delivering a POI to a subject or cell comprising expressing the POI in a VLP comprising L polypeptide from an avian hepadnavirus such as DHBV or a functional derivative or homolog thereof such that at least part of the POI is expressed on the surface of the VLP. In one aspect, the VLP is generated in an in vitro expression system. In another aspect, the VLP is generated in vivo. Where the POI is an antigenic polypeptide, the preferred cells are cells of the immune system such as antigen presenting cells.

Complementary forms of all or part the nucleic acid molecules of the present invention are expressly contemplated.

The terms "nucleic acids", "nucleotide" and "polynucleotide" include RNA, cDNA, genomic DNA, synthetic forms and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog (such as the morpholine ring), internucleotide modifications such as uncharged linkages (e.g. methyl phosphonates, phosphotriesters, phosphoamidates, carbamates, etc.), charged linkages (e.g. phosphorothioates, phosphorodithioates, etc.), pendent moieties (e.g. polypeptides), intercalators (e.g. acridine, psoralen, etc.), chelators, alkylators and modified linkages (e.g. α-anomeric nucleic acids, etc.). Also included are synthetic molecules that mimic polynucleotides in their ability to bind to a designated sequence via hydrogen binding and other chemical interactions. Such molecules are known in the art and include, for example, those in which peptide linkages substitute for phosphate linkages in the backbone of the molecule.

The term "similarity" as used herein includes exact identity between compared sequences at the nucleotide or amino acid level. Where there is non-identity at the nucleotide level, "similarity" includes differences between sequences which result in different amino acids that are nevertheless related to each other at the structural, functional, biochemical and/or conformational levels.

Where there is non-identity at the amino acid level, "similarity" includes amino acids that are nevertheless related to each other at the structural, functional, biochemical and/or conformational levels. In a particularly preferred embodiment, nucleotide and sequence comparisons are made at the level of identity rather than similarity.

Terms used to describe sequence relationships between two or more polynucleotides or polypeptides include "reference sequence", "comparison window", "sequence similarity", "sequence identity", "percentage of sequence similarity", "percentage of sequence identity", "substantially similar" and "substantial identity". A "reference sequence" is at least 9 to 12 but frequently 15 to 18 and often at least 21 to 25 or above, such as 30 monomer units, inclusive of nucleotides and amino acid residues, in length. Because two polynucleotides may each comprise (1) a sequence (i.e. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous residues that is compared to a reference sequence. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerised implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as, for example, disclosed by Altschul et al, *Nucleic Acid Research,* 25:3389-3402, 1997. A detailed discussion of sequence analysis can be found in Unit 19.3 of Ausubel et al, supra.

The terms "sequence similarity" and "sequence identity" as used herein refers to the extent that sequences are identical or functionally or structurally similar on a nucleotide-by-nucleotide basis or an amino acid-by-amino acid basis over a window of comparison. Thus, a "percentage of sequence identity", for example, is calculated by comparing two optimally aligned sequences over the window of comparison, determining the number of positions at which the identical nucleic acid base (e.g. A, T, C, G, I) or the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity. Conservative amino acid changes may be considered to provide similar sequences but not identical sequences.

Particularly preferred nucleic acid molecules encode a particle-associating portion of an L polypeptide and comprise a contiguous sequence of nucleotides substantially as set forth in SEQ ID NO: 6 or SEQ ID NO: 8 or a nucleotide sequence having at least about 50% similarity to SEQ ID NO: 6 or SEQ ID NO: 8. Preferably, the % similarity is in relation to the sequence encoding a particle-associating portion of L polypeptide.

Furthermore, the present invention contemplates nucleic acid molecules encoding a particle-associating portion of an L polypeptide comprising a sequence of nucleotides substantially as set forth in SEQ ID NO: 6 or SEQ ID NO: 8 or a nucleotide sequence capable of hybridizing to SEQ ID NO: 6 or SEQ ID NO: 8 or a complementary form thereof under medium stringency conditions.

Functional derivatives of the instant nucleic acid molecules include fragments thereof or sequences having one or more nucleotide mutations or modifications.

Mutations include one or more nucleotide deletions, insertions or substitutions. Alternatively or in addition, derivatives may be modified by the addition of sequences or moieties to enhance function such as enhanced stability or activity or to introduce new activity. For example, modifications may comprise the addition of fusagenic agents to enhance membrane permeability, modifications to affect pre or post-transcriptional modifications events, or to generate fusion proteins comprising labels, tags and other modifications for identification, purification and so forth.

Functional derivatives of the subject nucleic acid molecules retain the ability of the parent molecule to encode a polypeptide having the particle assembly function of S polypeptide or the particle associating function of L polypeptide.

Fragments of the nucleic acid molecules may include parts or one or more portions thereof, which have the function of the parent.

Functional homologs of the instant nucleic acid sequences include orthologus gene sequences from different species which are related by common phylogenic decent and also gene sequences from other species which are similar to the instant nucleic acid molecules as a result of convergent evolution, wherein the homologs are functionally and structurally related to the instant nucleic acid sequences and are consequently readily identified and/or isolated by hybridization based methods or by sequence comparison with published genome databases. For example, the nucleotide sequence of approximately 20 avian hepadnaviruses are publicly available (Triyatni et al, *J. Gen. Virol*, 82:373-378, 2001).

Similarity at the nucleic acid level may be assessed in assays exploiting different stringency of hybridization conditions as is well known in the art and is, for example, described in Ausubel et al, supra.

Reference herein to stringent hybridization conditions preferably means conditions which permit selective hybridization or annealing between molecules which are substantially similar. The hybridization temperature composition and ionic strength of the hybridization solution which meet this criteria will vary depending upon a number of well characterized factors such as length, degree of complementarity and GC content. For longer sequences it is generally possible to calculate the expected melting point of duplex nucleic acid sequences under various conditions. Hybridization may be to all or part of the instant polynucleotides with the minimum length being sufficient to provide specificity and functionality of their encoded polypeptides.

Low stringency hybridization conditions includes and encompasses from at least about 0 to at least about 15% v/v formamide and from at least about 1 M to at least about 2 M salt for hybridization, and at least about 1 M to at least about 2 M salt for washing conditions. Generally, low stringency is at from about 25-30° C. to about 42° C. The temperature may be altered and higher temperatures used to replace formamide and/or to give alternative stringency conditions.

Medium stringency includes and encompasses from at least about 16% v/v to at least about 30% v/v formamide and from at least about 0.5 M to at least about 0.9 M salt for hybridization, and at least about 0.5 M to at least about 0.9 M salt for washing conditions. High stringency includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m=69.3+0.41$ (G+C %). However, the $T_m$ of a duplex DNA decreases by 1° C. with every increase of 1% in the number of mismatch base pairs (Bonner et al, 1974). Formamide is optional in these hybridization conditions. Accordingly, particularly preferred levels of stringency are defined as follows: low stringency is 6×SSC buffer, 0.1% w/v SDS at 25-42° C.; a moderate stringency is 2×SSC buffer, 0.1% w/v SDS at a temperature in the range 20° C. to 65° C.; high stringency is 0.1×SSC buffer, 0.1% w/v SDS at a temperature of at least 65° C.

The recombinant nucleic acid molecules of the present invention which are suitable for use in making recombinant VLPs may be introduced into vectors to facilitate VLP production.

Vectors, preferably contain cloning sites and are capable of autonomous replication in a defined host cell. Alternatively, the vector may integrate into the genome and replicate together with the chromosome into which it has been introduced. Vectors generally also include selection markers.

Examples of selectable markers include genes conferring resistance to compounds such as antibiotics, genes conferring the ability to grow on selected substrates, genes encoding proteins that produce detectable signals such as luminescence. A wide variety of such markers are known and available, including, for example, antibiotic resistance genes such as the neomycin resistance gene (neo) and the hygromycin resistance gene (hyg). Selectable markers also include genes conferring the ability to grow on certain media substrates such as the tk gene (thymidine kinase) or the hprt gene (hypoxanthine phosphoribosyltransferase) which confer the ability to grow on HAT medium (hypoxanthine, aminopterin and thymidine); and the bacterial gpt gene (guanine/xanthine phosphoribosyltransferase) which allows growth on MAX medium (mycophenolic acid, adenine and xanthine). Other selectable markers for use in mammalian cells and plasmids carrying a variety of selectable markers are described in Sambrook et al., *Molecular Cloning—A Laboratory Manual*, Cold Spring Harbour, N.Y., USA, 1990.

The selectable marker may depend on its own promoter for expression and the marker gene may not necessarily be derived from human genomes (e.g. prokaryotic marker genes may be used in human cells). However, it is preferable to replace the original promoter with transcriptional machinery known to function in the recipient cells. A large number of transcriptional initiation regions are available for such purposes including, for example, metallothionein promoters, thymidine kinase promoters, β-actin promoters, immunoglobulin promoters, SV40 promoters and human cytomegalovirus promoters. A widely used example is the pSV2-neo plasmid which has the bacterial neomycin phosphotransferase gene under control of the SV40 early promoter and confers in mammalian cells resistance to G418 (an antibiotic related to neomycin). A number of other variations may be employed to enhance expression of the selectable markers in animal cells, such as the addition of a poly(A) sequence and the addition of synthetic translation initiation sequences. Both constitutive and inducible promoters may be used.

The recombinant nucleic acid molecule for use in making a recombinant VLP are preferably in kit form to facilitate introduction of a nucleic acid molecule encoding a POI and particle assembly.

Another aspect of the present invention provides an expression vector comprising a sequence of nucleotides encoding a POI and at least a particle-associating portion of an L polypeptide of DHBV or a functional derivative or homolog thereof wherein said POI is capable of being expressed as a fusion polypeptide with said L polypeptide.

Another aspect of the present invention provides an expression vector comprising a sequence of nucleotides encoding a POI and at least a part of the S domain of an L polypeptide of DHBV or a functional derivative or homolog thereof wherein the POI is expressed within or at a location N terminal to the S-domain of the L polypeptide amino acid sequence or functional derivative of homolog thereof.

Preferably, the POI is expressed N terminally of the S domain of L polypeptide or within the pre-S domain of L polypeptide.

As will be understood by those skilled in the art, the nucleic acid molecules of the present invention may be further modified to ensure their suitability for expression in a range of cells, selection in vitro, suitability for cloning various POIs therein. Such techniques and strategies are well known to those skilled in the art and may be conveniently referred to in Ausbel et al, *Eds short protocols in Molecular Biology*, John Wiley and Sons, $5^{th}$ Edition, 2002 and/or Sambrook et al, supra.

To ensure expression, the nucleotide sequences encoding the POI and the L polypeptide components are operatively linked to one or more expression control sequences. Preferably the two or more such nucleotide sequences are in the same reading frame.

In one embodiment expression vectors are conveniently stably integrated into the genome of host cells and expression is driven by host cell promoters.

The present invention also extends to microorganisms or host cells transformed or transfected or otherwise comprising a nucleic acid molecules comprising a sequence of nucleotides encoding a POI and at least a particle-associating portion of an L polypeptide of DHBV or a functional derivative or homolog thereof. Yeast cells are particularly convenient host cells. Prokaryotic or eukaryotic host cells are advantageously used. Typically prokaryotic cells include *E. coli, Bacillis* sp and eukaryotic cells include yeast, fungi, mammalian and insect cells.

The present invention furthermore provides a composition comprising a virus-like particle derived from DHBV L and S polypeptide for use as a vaccine wherein the L polypeptide comprises one or more antigens of interest.

The present invention also relates to a vaccine comprising an antigen of interest expressed as a fusion protein with a particle-associating L polypeptide of DHBV or a functional derivative or homolog thereof, and an S polypeptide of DHBV wherein the S polypeptide and antigen-L polypeptide are assembled into a VLP, in admixture with a suitable pharmaceutically acceptable diluent or carrier. The vaccine may be lyophilized prior to use and may furthermore be admixed with suitable adjuvants. Accordingly the vaccine may be in kit form.

By "pharmaceutically acceptable" carrier, or diluent is meant a pharmaceutical vehicle comprised of a material that is not biologically or otherwise undesirable, i.e. the material may be administered to a subject along with the selected active agent without causing any or a substantial adverse reaction. Carriers may include excipients and other additives such as diluents, detergents, coloring agents, wetting or emusifying agents, pH buffering agents, preservatives, and the like.

The VLPs, and polypeptide nucleic acid molecules of the present invention can be formulated in pharmaceutical compositions which are prepared according to conventional pharmaceutical compounding techniques. See, for example, Remington's Pharmaceutical Sciences, $18^{th}$ Ed. (1990, Mack Publishing, Company, Easton, Pa., U.S.A.). The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g. topical, intravenous, oral, intrathecal, epineural or parenteral.

For oral administration, the compounds can be formulated into solid or liquid preparations such as capsules, pills, tablets, lozenges, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, International Patent Publication No. WO 96/11698.

For parenteral administration, the compound may be dissolved in a pharmaceutical carrier and administered as either a solution of a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in a therapeutically effective amount. The actual amount administered and the rate and time-course of administration will depend on the nature and severity of the condition being treated. Prescription of treatment, e.g. decisions on dosage, timing, etc. is within the responsibility of general practitioners or specialists and typically takes account of the disorder to be treated, the condition of the individual patient, the site of delivery, the method of administration and other factors known to practitioners. Examples of techniques and protocols can be found in Remington's Pharmaceutical Sciences, supra.

Alternatively, targeting therapies may be used to deliver the active agent more specifically to certain types of cell, by the use of targeting systems such as antibodies or cell specific ligands or specific nucleic acid molecules. Targeting may be desirable for a variety of reasons, e.g. if the agent is self-antigenic or if it would not otherwise be able to enter the target cells.

Instead of administering these agents directly, they could be produced in the target cell, e.g. in a viral vector such as described below or in a cell based delivery system such as described in U.S. Pat. No. 5,550,050 and International Patent Publication Nos. WO 92/19195, WO 94/25503, WO 95/01203, WO 95/05452, WO 96/02286, WO 96/02646, WO 96/40871, WO 96/40959 and WO 97/12635. The vector could be targeted to the target cells. The cell based delivery system is designed to be implanted in a patient's body at the desired target site and contains a coding sequence for the target agent. Alternatively, the agent could be administered in a precursor form for conversion to the active form by an activating agent produced in, or targeted to, the cells to be treated. See, for example, European Patent Application No. 0 425 731A and International Patent Publication No. WO 90/07936.

Vaccine composition may alternatively comprise nucleic acid molecules encoding the recombinant VLPs.

Gene transfer systems known in the art may be useful in the practice of genetic manipulation. These include viral and non-viral transfer methods. A number of viruses have been used as gene transfer vectors or as the basis for preparing gene transfer vectors, including papovaviruses (e.g. SV40, Madzak et al., *J. Gen. Virol.* 73: 1533-1536, 1992), adenovirus (Berkner, *Curr. Top. Microbiol. Immunol.* 158: 39-66, 1992; Berkner et al., *BioTechniques* 6, 616-629, 1988; Gorziglia and Kapikian, *J. Virol.* 66: 4407-4412, 1992; Quantin et al., *Proc. Natl. Acad. Sci. USA* 89: 2581-2584, 1992; Rosenfeld et al., *Cell* 68: 143-155, 1992; Wilkinson et al., *Nucleic Acids Res.* 20: 2233-2239, 1992; Stratford-Perricaudet et al., *Hum. Gene Ther.* 1: 241-256, 1990; Schneider et al., *Nature Genetics* 18: 180-183, 1998), vaccinia virus (Moss, *Cur. Top. Microbiol. Immunol.* 158: 25-38, 1992; Moss, *Proc. Natl. Acad. Sci. USA* 93: 11341-11348, 1996), adeno-associated virus (Muzyczka, *Curr. Top. Microbiol. Immunol.* 158: 97-129, 1992; Ohi et al., *Gene* 89: 279-282, 1990; Russell and Hirata, *Nature Genetics* 18: 323-328, 1998), herpesviruses including HSV and EBV (Margolskee, *Curr. Top., Microbiol. Immunol.* 158: 67-95, 1992; Johnson et al., *J. Virol.* 66: 2952-2965, 1992; Fink et al., *Hum. Gene Ther.* 3: 11-19, 1992; Breakefield and Geller, *Mol. Neurobiol.* 1. 339-371, 1987; Freese et al., *Biochem. Pharmacol.* 40: 2189-2199, 1990; Fink et al., *Ann. Rev. Neurosci.* 19: 265-287, 1996), lentiviruses (Naldini et al, *Science* 272: 263-267, 1996), Sindbis and Semliki Forest virus (Berglund et al., *Biotechnology* 11: 916-920, 1993) and retroviruses of avian (Bandyopadhyay and Temin, *Mol. Cell. Biol.* 4: 749-754, 1984; Petropoulos et al., *J. Viol.* 66: 3391-3397, 1992], murine [Miller, *Curr. Top. Microbiol. Immunol.* 158: 1-24, 1992; Miller et al., *Mol. Cell. Biol.* 5: 431-437, 1985; Sorge et al., *Mol. Cell. Biol.* 4: 1730-1737, 1984; Mann and Baltimore, *J. Virol.* 54: 401-407, 1985; Miller et al., *J. Virol.* 62: 4337-4345, 1988] and human [Shimada et al., *J. Clin. Invest.* 88. 1043-1047, 1991; Helseth et al., *J. Virol.* 64: 2416-2420, 1990; Page et al., *J. Virol.* 64: 5270-5276, 1990; Buchschacher and Panganiban, *J. Virol.* 66: 2731-2739, 1982] origin.

Non-viral gene transfer methods are known in the art such as chemical techniques including calcium phosphate co-precipitation, mechanical techniques, for example, microinjection, membrane fusion-mediated transfer via liposomes and direct DNA uptake and receptor-mediated DNA transfer. Viral-mediated gene transfer can be combined with direct in vivo gene transfer using liposome delivery, allowing one to direct the viralvectors to particular cells. Alternatively, the retroviral vector producer cell line can be injected into particular tissue. Injection of producer cells would then provide a continuous source of vector particles.

In an approach which combines biological and physical gene transfer methods, plasmid DNA of any size is combined with a polylysine-conjugated antibody specific to the adenovirus hexon protein and the resulting complex is bound to an adenovirus vector. The trimolecular complex is then used to infect cells. The adenovirus vector permits efficient binding, internalization and degradation of the endosome before the coupled DNA is damaged. For other techniques for the delivery of adenovirus based vectors, see U.S. Pat. No. 5,691,198.

Liposome/DNA complexes have been shown to be capable of mediating direct in vivo gene transfer. While in standard liposome preparations the gene transfer process is non-specific, localized in vivo uptake and expression have been reported in tumor deposits, for example, following direct in situ administration.

General methods for generating the viral particles of the present invention are well known to skilled practitioners.

The present invention provides a method of preparing a recombinant VLP said method comprising:
  i) cloning a nucleic acid molecule encoding a polypeptide of interest into an expression vector comprising a particle-associating portion of an L polypeptide of DHBV or a functional derivative or homolog thereof;
  ii) infecting or transfecting a suitable cell with the recombinant expression vector of step i) under conditions which allow protein expression and particle assembly with S polypeptide of DHBV or a functional derivative or homolog thereof;
  iii) recovering said virus-like particles from said cells.

Yeast cells, for example, will be transformed with L/POI and S expression plasmids. Preferably, expression is driven by a yeast promoter and expressed in yeast cells, such as a strain of *Saccharomyces*.

Another aspect of the present invention is directed to antibodies to the fusion polypeptides of the present invention. Antibodies may be monoclonal or polyclonal and technique for their manufacture are very well known. Antibodies which specifically recognise determinants of the fusion polypeptide of the present invention are particularly preferred.

The present invention is further described by the further non-limiting Examples.

EXAMPLE 1

Substitution of a.a.45-125 of DHBV preS with the N terminal 82 Amino Acids of the Ectodomain of HCV E2 by Fusion PCR Plasmid pCDL-E2.465 encodesa chimeric L protein consisting (from N to the C terminus) of DHBV L aa 1-4; HCV E2 aa 384 to 465; DHBV L aa 126 to 328. This represents an insertion of a protein of interest of 82 amino acids. Fusion PCR (overlap extension PCR) was used as described by Ho et al, *Gene*, 77:51, 1989. Overlapping primers were each paired with an outside primer complementary to the plus strand of pCDL-w.t. or the minus strand of HCV construct in 2 first round PCR reactions using pfu enzyme. The PCR products (153 bp from pCDL as template and 272 bp with the HCV template) from each reaction were purified using a Qiagen min elute kit and the two purified products used as the template for the fusion PCR reaction using the outside primers. The 578 bp fusion PCR product was purified and digested with Xma1, cutting at nt 1743 of the HCV primer sequence and with Aat II, cutting at nt 831 of DHBV L. The plasmid, pMDL-w.t., carrying unique Xma1 and Aat II sites in the DHBV preS coding sequence was used as vector. The digested PCR fragment and the large fragment of the cut vector were excised from an agarose gel and purified using a Prep-a-gene kit (Bio-Rad). Competent cells (DH5α cells) were transformed with the ligated plasmid and transformants selected from ampicillin plates.

Positive clones were detected by restriction enzyme digestion of purified DNA using a restriction site which is also present in the HCV E2 ectodomain sequence (Bsa1).

A Sal1/Xho 1 fragment of pMDL-E2 containing the E2 insert was subcloned into pCDL-w.t. (DHBV L expression plasmid with CMV promotor) using the same unique restriction sites (see FIG. 1). Bsa 1 digestion was used again to confirm the presence of the E2 insert in pCDL-E2.465. The CDL-E2.465 clone was also confirmed by sequencing, covering the region of preS-E2-preS and part of S to nucleotide 1581.

```
Outside Primers
P804
5' GGGCAACATCCAGCAAAATCAATGG 3'
(SEQ ID NO: 1 DHBV nt 804-828)

P-1719
5' GCTGCGGAATGGCTAAAAGGGCCCCGACC 3'
(SEQ ID NO: 2 HCV nt 1719-1749 with an XmaI RE
site inserted, shown underlined)

Overlapping Chimeric Primers (plain type = DHBV
preS; bold = HCV E2)

P1492 (refers to nt at start of E2 sequence)
CCAACACTAGATCACGAAACCCACGTCACCGGGG
(SEQ ID NO: 3)

P-1492
GGTTGTGATCTAGTGCTTTGGGTGCAGTGGCCCC
(SEQ ID NO: 4)

Templates:
pCDL-wt (DHBV L expression plasmid); p90/HCV
FL-longpU
```

EXAMPLE 2

Expression and Analysis of CDL-E2 in Avian Hepatoma (LMH) Cells

The avian hepatoma cell line, LMH was co-transfected with 5 μg each of pCDL-E2.465 and pCI-S (Gazina et al, *Virology* 242:266, 1998) using the dextran sulphate method (Grgacic et al, *J. Gen. Virol.* 79:2743, 1998). Day 3 post-transfection media were collected for assessment of exported particles and cells either processed for cytosolic fractionation and assessment of intracellular particle formation or isolation of microsomes for protease protection analysis or isolation of the membrane fraction for assessment of protein expression (Grgacic, *J. Gen. Virol.* 83:1635, 2002).

EXAMPLE 3

Isolation of Intracellular and Extracellular Particles (i) Extracellular particles: Media from transfected LMH cells was harvested day 3 post-transfection and clarified of non-adherent cells by centrifugation for 5 min at 2,000 rpm.

(ii) Intracellular particles: Cell monolayers were washed twice with PBS and harvested by scaping cells into 1 ml PBS. Harvested cells were freeze/thawed three times with vigorous vortexing upon thawing. The cytosol fraction (supernatant) was obtained by centrifugation for 1 min at 10,000 rpm in an Eppendorf centrifuge. This procedure has been used in this laboratory to release DHBV particles from transfected cells capable of infecting primary duck hepatocytes.

Particles in the clarified media or cytosol fraction were diluted to 6 ml with PBS and pelleted for 3 h at 38,000 rpm in an SW40 rotor (Beckman) through 3 ml of 20% sucrose onto a 2 ml 70% sucrose cushion. The fraction at the 20-70% interface was collected from the bottom, methanol precipitated for 16 h at −20° C. followed by separation on 13% SDS-PAGE and Western blotting.

As shown in FIG. 2D, Western Blot show that the E2.465/L chimera is assembled into particles. Intracellular particles were isolated from avian hepatoma (LMH) cells transfected with pCDL-E2.465 and pCI-S by freeze-thawing cells 3 times, centrifugation to obtain the cytosolic fraction for sedimentation of particles through 20% sucrose on to a 70% sucrose cushion at 38,000 r.p.m. (SW41 rotor Beckman). The particle fraction at the 20-70% sucrose interface was methanol precipitated prior to SDS-PAGE and analysis of envelope proteins by Western blotting.

EXAMPLE 4

Protease Protection Analysis

Microsomes were prepared according to the method of Prange and Streeck, *EMBO J.* 14:247, 1995 with modifications. Transfected LMH cells (two 30 mm diameter wells) were washed in cold Tris-buffered saline (TBS: 50 mM Tris-HCl, pH 7.5; 150 mM NaCl).

The monolayers in each well were incubated on ice with 0.4 ml 0.1× TBS for 10 minutes and then harvested by scraping, pooled and dispersed by drawing 5 times through a 26G needle. The homogenate was adjusted to 1× TBS with 5× TBS and centrifuged for 20 min at 2,500 rpm at 4° C. to remove unbroken cells and nuclei. The supernatant was removed and set aside while the pellet was again dispersed in 300 μl TBS and centrifuged as before.

Supernatants were pooled and layered onto 2.7 ml 250 mM sucrose in TBS and centrifuged for 30 min. at 38,000 rpm at 4° C. in an SW-60 rotor (Beckman). The microsomal pellets were washed once with TBS and resuspended in 65 μl TBS.

For trypsin protection analysis the microsomal preparation was divided into three 20 μl aliquots. One sample was left untreated while the remaining two were treated with 25 μg/ml of trypsin (TPCK treated; Worthington Biochem. Corp. NJ. USA) with or without 0.5% NP-40 for 1 h. on ice.

EXAMPLE 5

Western Blot Analysis

Proteins were separated by SDS-PAGE (13% acrylamide) and transferred to nitrocellulose membrane(Schleicher and Schüll) using a Trans-Blot SD semi-dry transfer cell (Biorad). Membranes were blocked for 1 h with 3% skim milk in PBS plus 0.3% Tween 20 (PBST). Membranes were probed with monoclonal anti-S (7C.12) (Pugh et al, *J. Virol.* 69:4814, 1995) for 1 h in 1% skim milk; PBST, then washed with PBST and probed with goat anti-mouse Ig:horse radish peroxidase (Amersham) in 1% skim milk PBST. After a final wash in PBST (3×10 min.) proteins bands were visualised by enhanced chemiluminescence (ECL) (Amersham).

As shown in FIG. 2C, Western Blot show that the E2.465/L chimera is translocated across the ER. Protease protection analysis of ER microsomes prepared from LMH cells transfected with pCDL-E2.465 and pCI-S (an S protein expression plasmid). Microsomes samples were subjected to digestion with trypsin in the absence or presence of the detergent, NP-40, or left untreated, as denoted above each lane. Protease protection of E2.465/L chains was analysed by SDS-PAGE and Western blotting with a monoclonal anti-S antibody, which detects both E2.465/L and S proteins. Protection of E2.465/L from trypsin digestion (middle lane) is an indication of translocation to the ER lumen.

EXAMPLE 6

Construction of Strategically Selected Chimeric DHBV VLPs to Define Their carrying Capacity as a Potential Vaccine Delivery Vehicle The receptor binding region as well as the C terminus of preS is exposed to the DHBV subviral particle surface. These exposed regions, flanked by the membrane spanning S domain, are believed to be further stabilised through anchorage at the N terminus by the myristylation signal. The HCV E2 ectodomain inserted into this region of preS was similarly exposed and stabilised. PreS sequences are substituted by equivalent or larger sized foreign sequences or alternatively fused in frame to the N terminus of the S domain of L by fusion PCR.

To aid translocation of the chimeric L polypeptides, an L construct with a signal sequence such as the preprolactin signal sequence fused to the N terminus, which causes co-translational translocation of L, is also used. These SigL chains can assemble with S subunits and be exported as particles. Translocation of the chimeric preS domains is monitored by the protease protection assay and antibody mapping of the topology on the assembled particle by immunoprecipitation. Particles are purified by sucrose gradient sedimentation and analysed by EM/immunogold labelling for VLP formation. Pulse-chase metabolic labelling are performed to assess that the proportion of recombinant chains relative to S (approximately 1:4 for wild type DHBV) is maintained in the assembled particle.

EXAMPLE 7

Figure 5:
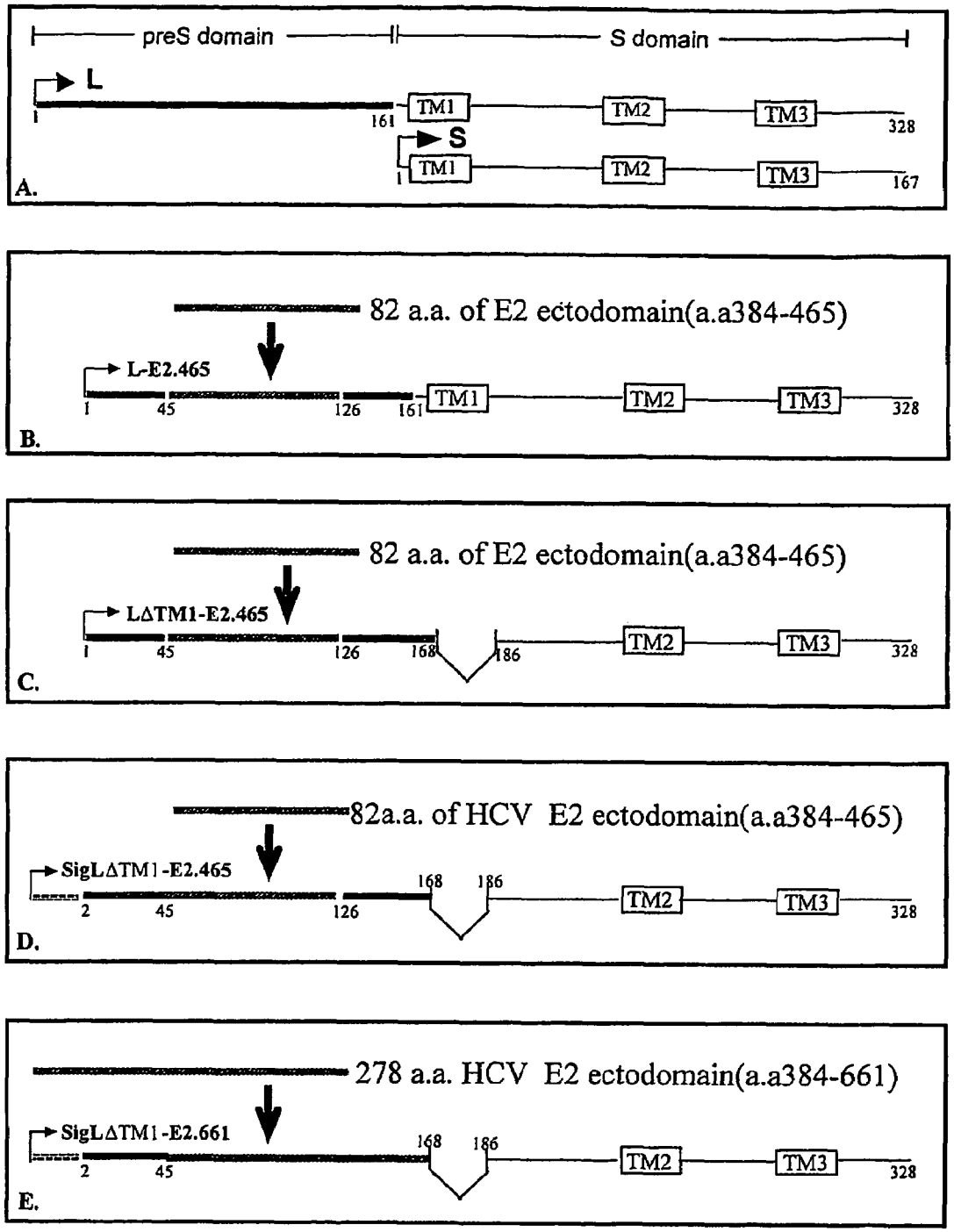
Figure 5:
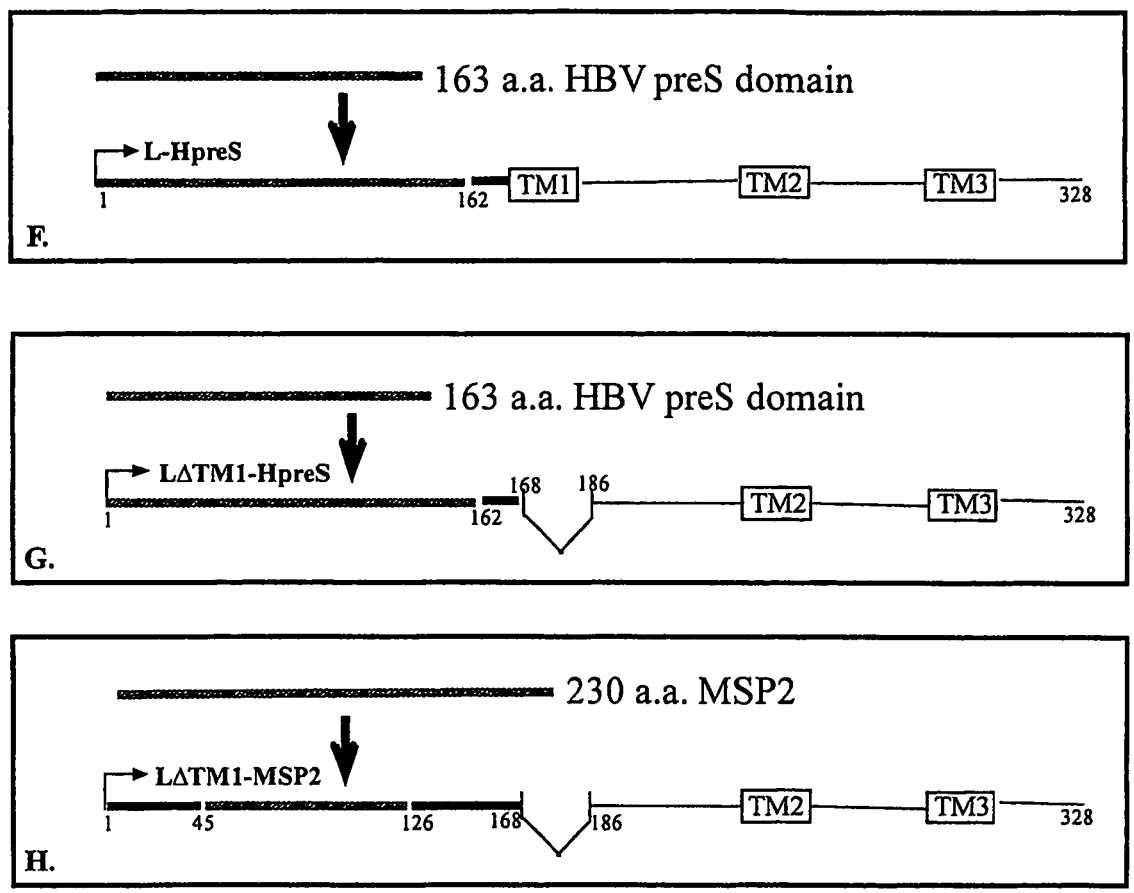

Construction and Analysis of the E2.465/L Chimera with TM1 Deleted in L pCDLΔTM1-E2.465 encodes a chimeric L protein consisting (from the N to the C terminus) of DHBV L a.a. 1-45; HCV E2 a.a. 384-465; DHBV L a.a.126-328 with a deletion of 18 a.a. of transmembrane domain 1 at a.a.168-186 (see FIG. 5B). This represents an insertion of a protein of interest of 82 a.a.

pCDLΔTM1-E2.465 was constructed by subcloning a Sal 1/BstEII fragment (encompassing preS/E2 and S domain sequences) of pMDLΔTM1-E2.465 into pCDL-w.t. Transfer of the insert was confirmed by restriction enzyme digestion with Bsa 1. Expression and analysis of pCDLΔTM1-E2.465 was done in LMH cells as described in Examples 2, 3 and 4. Expression of the E2;465/LΔTM1 chimera both as protein and as assembled particles, was greater than that observed with the pCDL-E2.465 plasmid. Constructs with the TM1 deletion can be used for all chimeric DHBV VLPs, if required.

EXAMPLE 8

Construction of an E2.465/LΔTM1 Chimera with an N Terminal Signal Sequence (Preprolactin)

pSigLΔTM1-E2.465 encodes a chimeric L protein consisting (from the N to the C terminus) Preprolactin signal sequence a.a.1-26; DHBV L a.a. 2-45; HCV E2 a.a. 384-465; DHBV L a.a.126-328 with a deletion of 18 a.a. of transmembrane domain 1 at a.a.168-186 (see FIG. 5D). This represents an insertion of a protein of interest of 82 amino acids.

Signal sequences fused to the N terminus of DHBV L cause the L protein to be co-translationally translocated across the ER membrane which in turn results in glycosylation of the L protein (Swaymeye and Schaller, *J. Virol.*, 71:9434, 1997; Gazina et al, (supra)).

Firstly, pCDSigLΔTM1-E2.465 was constructed by sequential subcloning, first of an AatII/Kpn 1 fragment of pMDLΔTM1-E2.465 into pMDSigLΔTM1-E2.465 and then a Sal 1/BstEII fragment of the latter into pCDSigLΔ PpuMul/BstEII fragment from pCDSigLΔTM1-E2.465 containing the E2.465 sequences was subcloned into the same sites in PPL-L, encoding the preprolactin signal sequence at the N terminus of DHBV L (Gazina et al, (supra)). The resulting plasmid was assigned the name, pSigLΔTM1-E2.465. pSigLΔTM1-E2.465 expressed the chimeric L-E2.465 protein at similar levels to the PPL-L protein when examined as in Example 2.

EXAMPLE 9

Construction and Analysis of the E2.661/L Chimera Comprising the Entire Ectodomain of HCV E2 pSigLΔTM1-E2.661 encodes a chimeric L protein consisting (from the N to the C terminus) Preprolactin signal sequence a.a.1-26; DHBV L a.a. 2-45; HCV E2 a.a. 384-661; DHBV L a.a.168-328 (see FIG. 5E). This represents an insertion of a protein of interest of 278 amino acids.

The E2.661/L chimera incorporates a.a. 384-661 of HCV E2, i.e., the 278 amino acid ectodomain of E2 into the preS domain of DHBV L. The E2.661/L was constructed by PCR using a primer to the sequence at the start site if HCV E2 (nt 1490) and reverse primer covering nt 2321 at the end of the ectodomain of E2 and incorporating a Kpn 1 restriction enzyme site. The PCR product was digested with Nae 1 (nt 1517 of E2) and Kpn 1 and inserted into the same sites in pCDLΔTM1-E2.465 to create pCDLΔTM1-E2.661. Incorporation of the PPL signal sequence to this construct was done by a three-way ligation of the following fragments: a Nar1/BstE II fragment of pCDLΔTM1-E2.661 encompassing the E2 sequence; a Bgl II/Nar 1 fragment of the pSigLΔTM1-E2.465 encompassing the preprolactin sequence and part of E2 and a Bgl II/BstE II fragment of PPL-L providing the remaining vector sequences. Expression of the resulting construct pSigLΔTM1-E2.661 was shown in LMH cells as described in Example 2 (see FIG. 6A).

EXAMPLE 10

Construction and Analysis of HBVpreS/L and HBVpreS/LΔ Chimeras pCDL-HBVpreS encodes a chimeric L protein consisting (from the N to the C terminus) of HBV preS a.a. 1-163; DHBV L a.a.162 -328. pCDLΔ-HBVpreS encodes a chimeric L protein consisting (from the N to the C terminus) of HBV preS a.a. 1-163; DHBV L a.a.162 -328 with a deletion of 18 a.a. of transmembrane domain 1 at a.a.168-186 (see FIG. 5F to 5G). These constructs represents an insertion of a protein of interest of 163 amino acids.

Genome sequences encoding the preS domain (a.a.1-163) of HBV (strain ayw) and the S domain of DHBV were amplified by PCR from plasmids encoding the respective L proteins, then joined by fusion PCR. The HBV preS primer introduced a Sal 1 restriction site upstream of the initiation of HBV preS. The fusion PCR product was digested using Sal 1 and a BstEII restriction site in the DHBV sequence upstream of the DHBV primer and ligated into the same sites in pCDL-w.t. to create the pCDL-HBVpreS plasmid. The HBV preS sequence, which has no sequence homology with the DHBV preS (Sprengel et al, *J. Med. Virol.*, 15:323, 1985), is thus directly fused to the S domain of DHBV L in these constructs.

pCDLΔ-HBVpreS was constructed by a three-way ligation of the following fragments: a Sal1/Kpn1 fragment of pCDL-HBVpreS encompassing the HBV preS sequence, a Kpn1/BstEII fragment of pCDLΔTM1 encompassing the DTM1 region and a Sal 1/BstEII fragment of pCDL-w.t. providing the remaining vector sequences.

Expression and analysis of pCDL-HBVpreS and pCDLΔ-HBVpreS was done in LMH cells as described in Examples 2, 3 and 4.

EXAMPLE 11

Construction and Analysis of the *P. falciparum* MSP2/LΔTM1 Chimera pCDLΔTM1-MSP2 encodes a chimeric L protein consisting (from the N to the C terminus) of DHBV L a.a.1-30; *P. falciparum* MSP2 a.a. 20-249; DHBV L a.a.126-328 with a deletion of 18 a.a. of transmembrane domain 1 at a.a.168-186 (see FIG. 5H). This represents an insertion of a protein of interest of 230 amino acids.

The malaria pathogen, *Plasmodium falciparum* (isolate NF54 clone 3D7) MSP2 gene was cloned by fusion PCR. Two sets of primers were used for generating separate templates for fusion. The first set encompassed a forward primer incorporating the SalI restriction enzyme site of pCDLΔTM1 and a reverse primer overlapping the first 27 bp of MSP2 and the second set consisted of a forward primer overlapping DHBV L and a reverse primer incorporating a XmaI restriction enzyme site into MSP2. The separate templates were then joined by fusion PCR, restricted by SalI and XmaI and ligated into the vector. The ligated insert-vector was transformed into *E. coli* DH5 alpha, creating the chimeric vector pCDL ΔTM1-MSP2. Expression of the resulting construct was shown in LMH cells as described in Example 2 (see FIG. 6B).

EXAMPLE 12

Production of DHBV VLPs in *Saccharomyces cerevisiae*

For the purposes of scaling-up production of recombinant DHBV VLPs and chimeric DHBV VLPs for immunisation studies, a yeast inducible expression system was used. DHBV DNA encoding the large envelope protein was cloned into the pYES2 vector (Invitrogen) by PCR using a primer to the sequence upstream (starting at nt 762) of the start site of DHBV L (nt 801) and incorporating a Sac 1 restriction enzyme site and a reverse primer covering nucleotide 1910 and incorporating an Eco R1 restriction site. The PCR product was digested and inserted into the Sac1 and EcoR1 sites in the multicloning site of the vector. The pYES2 vector carries an ampicillin resistance gene for selection of clones in *E. coli*. Clones containing the DHBV L gene (pYES-DL) were confirmed by restriction enzyme digestion and one was selected for transformation of the yeast strain, INVSc1.

A yeast expression plasmid for DHBV S gene expression, pMB-DS (Klingmüller and Schaller, *J. Virology*, 67:7414, 1993), was used for co-transformation of the NVSc1 strain with pYES-DL. The pYES2 vector carries a URA3 gene for selection of transformants in yeast and pMB-DS carries a LEU2 selection marker. The INVSC-1 stain used will not grow in media deficient in leucine, uracil, histidine and tryptophan. Co-transformants were therefore selected for growth on media lacking both leucine and uracil. Transformation of competent INVSc-1 cells was done according to the manufacturer's (INVITROGEN) instructions. Both plasmids have a GAL1 promoter for high level inducible protein expression in yeast by galactose and repression by glucose. Transformants were grown in yeast synthetic drop-out media without uracil and leucine (SC-UL) with 2% glucose for 2 days and then induced for protein expression by the substitution of glucose with 2% galactose and grown in YEP (1% yeast extract; 2% peptone) media for a further 24-48 hours.

DHBV L and S protein expression was examined by Western blotting following extraction of protein in yeast cells with acid-washed glass beads and vigorous vortexing followed by centrifugation. Supernatants were analysed by Western blotting with anti-S monoclonal as described in Example 5. Transformants (DL/S), which expressed the greatest amount of L and S protein were selected and stored as glycerol stocks.

For analysis of DHBV VLP production: A 50 ml yeast culture of DL/S was extracted and the supernatant loaded onto 20% sucrose above a 70% sucrose cushion and centrifuged at 38,000 rpm for 3 hours in a SW41 rotor (Beckman). The fraction at the 20-70% interface was then loaded onto a 20-70% sucrose step gradient and centrifuge for 5 hours at 38,000 rpm (Grgacic and Schaller, *J. Virol.*, 74:5116, 2000). Fractions were collected from the bottom of the gradient and analysed by Western blotting. Serum-derived DHBV subviral particles sediment at approximately 30% sucrose (peak fractions 7 and 8). The yeast-derived DHBV VLPs were similarly shown to sediment largely at 30% sucrose (see FIG. 7A).

Transmission Electron Microscopy (TEM) of yeast-derived particles was conducted by the Monash Micro Imaging Facility. Particles for TEM were sucrose gradient purified and further buffer exchanged with phosphate buffered saline using a Vivaspin 20 desalting and concentration device (Vivascience) prior to negative staining with uranyl acetate. A comparison of TEM of serum-derived DHBV subviral particles and yeast-derived DL/S particles showed similar particle morphology and size (approx 40-60 nm).

Variations on the pYES-DL construct to include the deletion in transmembrane domain 1 and the preprolactin Signal sequence with and without the deletion in transmembrane domain 1 were made. pYES-DLΔTM1 was constructed by subcloning an Aat II/Bst EII fragment of pMDLΔTM1 containing the region of the TM1 deletion into pYES-DL using the same restriction enzyme sites. pYES-SigL was constructed by subcloning a Sac 1/Bst EII fragment of PPL-L containing the signal sequence into pYES-DL using the same restriction sites. pYESSigLΔTM1 was constructed by subcloning an Aat II/BST Eii fragment of pMDLΔTM1 containing the TM1 deleted region into pYES-SigL using the same restriction sites. VLP production and analysis in yeast was done as described above. DLΔTM1/S, SigL/S and SigLΔTM1/S VLPs were shown to have the same sedimentation profile as DL/S particles in a sucrose step gradient.

EXAMPLE 13

Production of Chimeric DHBV VLPs in *Saccharomyces cerevisiae* pYES-DL-E2.465 and pYES-DLΔTM1-E2.465 were constructed by subcloning E2 encompassing sequences from pMDLΔTM1-E2.465 in an Aat II/Xma1 fragment for the former and an Aat II/Bst EII fragment for the latter into the same sites in pYES-DL. INVSc-1 cell were co-transformed with either pYES-DL-E2.465 and pMB-DS or pYES-DLΔTM1-E2.465 and pMB-DS for chimeric particle production and analysis in yeast as described in Example 11. The DLΔTM1-E2.465 VLPs were shown to have the same sedimentation profile as DL/S particles in a sucrose step gradient (see FIG. 7B) and have a similar morphology to DL/S particles by TEM.

pYES-DLΔTM1-HpreS was constructed by PCR using a primer to the sequence upstream (starting at nt 4091) of the start site of HBV preS (nt 4138) and incorporating a Sac 1 restriction enzyme site and a reverse primer covering nucleotide 1910 of the DHBV sequence and incorporating an Eco R1 restriction site. The PCR product was digested and inserted into the Sac1 and EcoR1 sites in the multicloning site of the PYES vector. Chimeric particle production and analysis in yeast was done as described in Example 11. DLΔTM1-HpreS VLPs were shown to have the same sedimentation profile as DL/S particles in a sucrose step gradient (see FIG. 7C) and have a similar morphology to DL/S particles by TEM.

EXAMPLE 14

Analysis of Immunogenicity of DHBV VLPs Produced in Yeast

DL/S VLPs were used to immunize rats. DL/S VLP production: A 100 ml yeast culture of DL/S was extracted and the supernatant loaded onto two 20% sucrose above a 70% sucrose cushion and centrifuged at 38,000 rpm for 3 hours in a SW41 rotor (Beckman). The portion of the pelleted VLPs was examined by SDS-PAGE and Coomassie Brilliant Blue protein staining against a standard protein to estimate the amount of VLP protein. Approximately 10 µg doses of DL/S in a total of 200 µl were injected in rats i.m. Rats were put into three groups of six rats with each group receiving DL/S VLPs either without the addition of an adjuvant or with the addition of alum or Titremax. Rats were bled 3 weeks following immunisation and subsequent boosts. Analysis of rat sera by Western blotting of DHBV L/S protein showed a strong and rapid immunoreactivty without the presence of adjuvant to the DHBV L protein with little or no response to DHBV S protein (see FIG. 8).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Altschul et al, *Nucleic Acid Research*, 25:3389-3402, 1997.
Ausbel et al, Eds *short protocols in Molecular Biology*, John Wiley and Sons, 5th Edition, 2002.
Bandyopadhyay and Temin, *Mol. Cell. Biol.* 4: 749-754, 1984.
Berglund et al., *Biotechnology* 11: 916-920, 1993.
Berkner et al., *BioTechniques* 6: 616-629, 1988.
Berkner, *Curr. Top. Microbiol. Immunol.* 158: 39-66, 1992.
Bisht, H., D. A. Chugh, M. Raje, S. Swaminathan, and N. Khanna. *J. Biotechnology.* 99:97-110, 2002.
Bonner et al, Functional organisation of the mammalian genome CSHSQB, 38:308-10, 1974.
Breakefield and Geller, *Mol. Neurobiol.* 1: 339-371, 1987.
Bruss, V., and D. Ganem. *J. Virol.* 65:3813-3820, 1991.
Bruss et al., *EMBO J.*, 13:2273-2279, 1994.
Buchschacher and Panganiban, *J. Virol.* 66: 2731-2739, 1982.
Delpeyroux, F., N. Chenciner, A. Lim, M. Lambert, Y. Malpiece, and R. E. Streek. *J Mol. Biol.* 195:343-350, 1987.
Fink et al., *Ann. Rev. Neurosci.* 19: 265-287, 1996.
Fink et al., *Hum. Gene Ther.* 3: 11-19, 1992.
Frazer, I. *Virus Research.* 89:271-274, 2002.
Freese et al., *Biochem. Pharmacol.* 40: 2189-2199, 1990.
Gazina et al, *Virology* 242:266, 1998.
Gorziglia and Kapikian, *J. Virol.* 66: 4407-4412, 1992.
Grgacic et al, *J. Gen. Virol.* 79:2743, 1998.
Grgacic, *J. Gen. Virol.* 83:1635, 2002.
Grgacic and Schaller, *J. Virol.*, 74:5116, 2000.
Helseth et al., *J. Virol.* 64: 2416-2420, 1990.
Ho et al, *Gene,* 77:51, 1989.
Johnson et al., *J. Virol.* 66: 2952-2965, 1992.
Klingmuller, U., and H. Schaller. *J. Virol.* 67:7414-7422, 1993.
Krueger, D. H., R. Ulrich, and W. H. Gerlich. *Biol. Chem.* 380:275-276, 1998.
Lenhoff, R., and J. Summers. *J. Virol.* 68:4565-4571, 1994.
Madzak et al., *J. Gen. Virol.* 73: 1533-1536, 1992.
Mann and Baltimore, *J. Virol.* 54: 401-407, 1985.
Margolskee, *Curr. Top., Microbiol. Immunol.* 158: 67-95, 1992.
Miller et al., *J. Virol.* 62: 4337-4345, 1988.
Miller et al., *Mol. Cell. Biol.* 5: 431437, 1985.
Miller, *Curr. Top. Microbiol. Immunol.* 158:1-24, 1992.
Moss, *Curr. Top. Microbiol. Immunol.* 158: 25-38, 1992.
Moss, *Proc. Natl. Acad. Sci. USA* 93: 11341-11348, 1996.
Muzyczka, *Curr. Top. Microbiol. Immunol.* 158: 97-129, 1992.
Naldini et al., *Science* 272: 263-267, 1996.
Nassal, M. *Curr. Top. Microbiol. Immunol.* 214:297-337, 1996.
Netter, H. J., T. B. MacNaughton, W.-P. Woo, R. Tindle, and E. J. Gowans. *J Virol.* 75:2130-2141, 2001.
Ohi et al., *Gene* 89: 279-282, 1990.
Page et al., *J. Virol.* 64: 5270-5276, 1990.
Petropoulos et al., *J. Viol.* 66: 3391-3397, 1992.
Pugh et al, *J. Virol.* 69:4814, 1995.
Prange, R., M. Werr, M. Birkner, R. Hilfich, and R. E. Streeck. *J. Gen. Virol.* 76:2131-2140, 1995.
Prange and Streeck, *EMBO J.* 14:247, 1995.
Quantin et al., *Proc. Natl. Acad. Sci. USA* 89: 2581-2584, 1992.
Rosenfeld et al., *Cell* 68: 143-155, 1992.
Russell and Hirata, *Nature Genetics* 18: 323-328, 1998.
Sambrook et al. "Molecular Cloning: A Laboratory Manual" Cold Spring Harbor Laboratory, 3rd Edition, 2001.
Schneider et al., *Nature Genetics* 18: 180-183, 1998.
Shimada et al., *J. Clin. Invest.* 88: 1043-1047, 1991.
Sorge et al., *Mol. Cell. Biol.* 4: 1730-1737, 1984.
Sprengel et al, *J. Med. Virol.*, 15:323, 1985.
Stratford-Perricaudet et al., *Hum. Gene Ther.* 1: 241-256, 1990.
Swaymeye and Schaller, *J. Virol.* 71:9434, 1997.
Triyatni et al, *J. Gen. Virol,* 82:373-378, 2001.
Wilkinson et al., *Nucleic Acids Res.* 20: 2233-2239, 1992.

The invention claimed is:

1. A fusion polypeptide comprising a polypeptide of interest (POI) fused to a particle-associating portion of a large envelope polypeptide (L) of an avian hepadnavirus wherein the POI is not a pre-S region of an avian hepadnavirus and is located N-terminally to said particle-associating portion of the L polypeptide, and wherein the particle-associating portion consists of a fragment of the L polypeptide, wherein said fragment is (i) the S domain, (ii) the S domain minus the TM1 domain, or (iii) a portion of the L polypeptide which is downstream of TM1 and comprises at least TM2, the 5' cysteine loop between TM1 and TM2, and the sequence downstream of TM2.

2. The polypeptide of claim 1 wherein the particle-associating portion of L polypeptide consists of the amino acid sequence as set forth in SEQ ID NO: 9 or amino acid sequence having at least 90% identity to SEQ ID NO: 9 (S domain of L).

3. The polypeptide of claim 1 wherein the particle-associating portion of L-polypeptide consists of amino acids 24 to 167 of SEQ ID NO: 9 or an amino acid sequence having at least 90% identity thereto.

4. The polypeptide of claim 1 wherein said particle-associating portion thereof is encoded by the sequence of nucleotides as set forth in SEQ ID NO: 8 or having at least about 90% identity to SEQ ID NO: 8.

5. The polypeptide according to claim 1 wherein said fusion protein further comprises a signal sequence.

6. The polypeptide of claim 1 wherein the L polypeptide is a DHBV L polypeptide.

* * * * *

SEQUENCE LISTING

<160> NUMBER OF SEQ ID NOS: 13

<210> SEQ ID NO 1
<211> LENGTH: 25
<212> TYPE: DNA
<213> ORGANISM: duck

<400> SEQUENCE: 1
gggcaacatc cagcaaaatc aatgg                                           25

<210> SEQ ID NO 2
<211> LENGTH: 30
<212> TYPE: DNA
<213> ORGANISM: Homo sapiens

<400> SEQUENCE: 2
gctgcggaat ggctaaaagg gcccccgacc                                      30

<210> SEQ ID NO 3
<211> LENGTH: 34
<212> TYPE: DNA
<213> ORGANISM: Homo sapiens

<400> SEQUENCE: 3
ccaacactag atcacgaaac ccacgtcacc gggg                                 34

<210> SEQ ID NO 4
<211> LENGTH: 34
<212> TYPE: DNA
<213> ORGANISM: Homo sapiens

<400> SEQUENCE: 4
ggttgtgatc tagtgctttg ggtgcagtgg cccc                                 34

<210> SEQ ID NO 5
<211> LENGTH: 3021
<212> TYPE: DNA
<213> ORGANISM: duck

<400> SEQUENCE: 5
catgctcatt tgaaagctta tgcaaaaatt aacgaggaat cactggatag ggctaggaga      60
ttgctttggt ggcattacaa ctgtttactg tggggagaag ctcaagttac taactatatt     120
tctcgtttgc gtacttggtt gtcaactcct gagaaatata gaggtagaga tgccccgacc     180
attgaagcaa tcactagacc aatccaggtg gctcagggag cagaaaaac aactacgggt      240 actagaaaac ctcgtggact cgaacctaga agaagaaaag ttaaaaccac agttgtctat     300
gggagaagac gttcaaagtc ccgggaaagg agagccccta caccccaacg tgcgggctcc     360
cctctcccac gtagttcgag cagccaccat agatctccct cgcctaggaa ataaattacc     420
tgctaggcat cacttaggta aattgtcagg actatatcaa atgaagggct gtactttttaa    480 cccagaatgg aaagtaccag atatttcgga tactcatttt aatttagatg tagttaatga     540
gtgcccttcc cgaaattgga atatttgac tccagccaaa ttctggccca agagcatttc      600
ctactttcct gtccaggtag gggttaaacc aaagtatcct gacaatgtga tgcaacatga     660
atcaatagta ggtaaatatt taaccaggct ctatgaagca ggaatccttt ataagcggat     720
atctaaacat ttggtcacat ttaaaggtca gccttataat tgggaacagc aacaccttgt     780
caatcaacat cacatttatg atggggcaac atccagcaaa atcaatggac gtcagacgga     840

-continued

```
tagaaggagg agaaatactg ttaaaccaac ttgccggaag gatgatccca aaagggactt    900
tgacatggtc aggcaagttt ccaacactag atcacgtgtt agaccatgtg caaacaatgg    960
aggagataaa caccctccag aatcagggag cttggcctgc tggggcggga aggagagtag   1020
gattatcaaa tccgactcct caagagattc ctcagcccca gtggactccc gaggaagacc   1080
aaaaagcacg cgaagctttt cgccgttatc aagaagaaag accaccggaa accaccacca   1140
ttcctccgtc ttcccctcct cagtggaagc tacaacccgg ggacgatcca ctcctgggaa   1200
atcagtctct cctcgagact catccgctat accagtcaga accagcggtg ccagtgataa   1260
aaactccccc cttgaagaag aaaatgtctg gtaccttcgg gggaatacta gctggcctaa   1320
tcggattact ggtaagcttt tcttgttga taaaaattct agaaatactg aggaggctag   1380
attggtggtg gatttctctc agttctccaa agggaaaaat gcaatgcgct ttccaagata   1440
ctggagccca aatctctcca cattacgtag gatcttgccc gtggggatgc ccaggatttc   1500
tttggaccta tctcaggctt tttatcatct tcctcttaat cctgctagta gcagcaggct   1560
tgctgtatct gacggacaac gggtctacta ttttaggaaa gctccaatgg gcgtcggtct   1620
cagcccttt ctcctccatc tcttcactac tgccctcgga tccgaaatct ctcgtcgctt   1680
taacgtttgg actttcactt atatggatga cttcctcctc tgccacccaa acgctcgtca   1740
ccttaacgca attagccacg ctgtctgctc ttttttacaa gagttaggaa taagaataaa   1800
ctttgacaaa accacgcctt ctccggtgaa tgaaataaga ttcctcggtt accagattga   1860
tgaaaatttc atgaagattg aagaaagcag atggaaagaa ttaaggactg taatcaagaa   1920
aataaaagta ggagaatggt atgactggaa atgtattcaa agatttgtgg ggcatttgaa   1980
ttttgttttg cctttactaa aaggtaatat tgaaatgtta aaaccaatgt atgctgctat   2040
tactaaccaa gtaaacttta gcttctcttc atcctatagg actttgttat ataaactaac   2100
aatgggtgtg tgtaaattaa gaataaagcc aaagtcctct gtacctttgc cacgtgtagc   2160
tacagatgct accccaacac atggcgcaat atcccatatc accggcggga gcgcagtgtt   2220
tgcttttttca aaggtcagag atatacatgt tcaggaacta ttgatgtctt gtttagccaa   2280
gataatgatt aaaccacgtt gtctcttatc tgattcaact tttgtttgcc ataagcgtta   2340
tcagacgtta ccatggcatt tgctatgtt ggccaaacaa ttgctcaaac cgatacaatt   2400
gtactttgtc ccgagcaaat ataatcctgc tgacggccca tccaggcaca aacctcctga   2460
ttggacggct tttccataca cccctctctc gaaagcaata tatattccac ataggctatg   2520
tggaacttaa gaattacacc cctctccttc ggagctgctt gccaaggtat ctttacgtct   2580
acattgctgt tgtcgtgtgt gactgtacct ttggtatgta ccattgttta tgattcttgc   2640
ttatatatgg atatcaatgc ttctagagcc ttagccaatg tgtatgatct accagatgat   2700
ttctttccaa aaatagatga tcttgttaga gatgctaaag acgctttaga gccttattgg   2760
aaatcagatt caataaagaa acatgttttg attgcaactc actttgtgga tctcattgaa   2820
gacttctggc agactacaca gggcatgcat gaaatagccg aatcattaag agctgttata   2880
cctcccacta ctactcctgt tccaccgggt tatcttattc agcacgagga agctgaagag   2940
ataccttggg gagatttatt taaacaccaa gaagaaagga tagtaagttt ccaacccgac   3000
tatccgatta cggctagaat t                                             3021
```

<210> SEQ ID NO 6
<211> LENGTH: 984
<212> TYPE: DNA

<213> ORGANISM: duck
<220> FEATURE:
<221> NAME/KEY: CDS
<222> LOCATION: (1)..(984)

<400> SEQUENCE: 6

```
atg ggg caa cat cca gca aaa tca atg gac gtc aga cgg ata gaa gga      48
Met Gly Gln His Pro Ala Lys Ser Met Asp Val Arg Arg Ile Glu Gly
1               5                   10                  15 gga gaa ata ctg tta aac caa ctt gcc gga agg atg atc cca aaa ggg      96
Gly Glu Ile Leu Leu Asn Gln Leu Ala Gly Arg Met Ile Pro Lys Gly
            20                  25                  30 act ttg aca tgg tca ggc aag ttt cca aca cta gat cac gtg tta gac     144
Thr Leu Thr Trp Ser Gly Lys Phe Pro Thr Leu Asp His Val Leu Asp
        35                  40                  45 cat gtg caa aca atg gag gag ata aac acc ctc cag aat cag gga gct     192
His Val Gln Thr Met Glu Glu Ile Asn Thr Leu Gln Asn Gln Gly Ala
    50                  55                  60 tgg cct gct ggg gcg gga agg aga gta gga tta tca aat ccg act cct     240
Trp Pro Ala Gly Ala Gly Arg Arg Val Gly Leu Ser Asn Pro Thr Pro
65                  70                  75                  80 caa gag att cct cag ccc cag tgg act ccc gag gaa gac caa aaa gca     288
Gln Glu Ile Pro Gln Pro Gln Trp Thr Pro Glu Glu Asp Gln Lys Ala
                85                  90                  95 cgc gaa gct ttt cgc cgt tat caa gaa gaa aga cca ccg gaa acc acc     336
Arg Glu Ala Phe Arg Arg Tyr Gln Glu Glu Arg Pro Pro Glu Thr Thr
            100                 105                 110 acc att cct ccg tct tcc cct cct cag tgg aag cta caa ccc ggg gac     384
Thr Ile Pro Pro Ser Ser Pro Pro Gln Trp Lys Leu Gln Pro Gly Asp
        115                 120                 125 gat cca ctc ctg gga aat cag tct ctc ctc gag act cat ccg cta tac     432
Asp Pro Leu Leu Gly Asn Gln Ser Leu Leu Glu Thr His Pro Leu Tyr
    130                 135                 140 cag tca gaa cca gcg gtg cca gtg ata aaa act ccc ccc ttg aag aag     480
Gln Ser Glu Pro Ala Val Pro Val Ile Lys Thr Pro Pro Leu Lys Lys
145                 150                 155                 160 aaa atg tct ggt acc ttc ggg gga ata cta gct ggc cta atc gga tta     528
Lys Met Ser Gly Thr Phe Gly Gly Ile Leu Ala Gly Leu Ile Gly Leu
                165                 170                 175 ctg gta agc ttt ttc ttg ttg ata aaa att cta gaa ata ctg agg agg     576
Leu Val Ser Phe Phe Leu Leu Ile Lys Ile Leu Glu Ile Leu Arg Arg
            180                 185                 190 cta gat tgg tgg tgg att tct ctc agt tct cca aag gga aaa atg caa     624
Leu Asp Trp Trp Trp Ile Ser Leu Ser Ser Pro Lys Gly Lys Met Gln
        195                 200                 205 tgc gct ttc caa gat act gga gcc caa atc tct cca cat tac gta gga     672
Cys Ala Phe Gln Asp Thr Gly Ala Gln Ile Ser Pro His Tyr Val Gly
    210                 215                 220 tct tgc ccg tgg gga tgc cca gga ttt ctt tgg acc tat ctc agg ctt     720
Ser Cys Pro Trp Gly Cys Pro Gly Phe Leu Trp Thr Tyr Leu Arg Leu
225                 230                 235                 240 ttt atc atc ttc ctc tta atc ctg cta gta gca gca ggc ttg ctg tat     768
Phe Ile Ile Phe Leu Leu Ile Leu Leu Val Ala Ala Gly Leu Leu Tyr
                245                 250                 255 ctg acg gac aac ggg tct act att tta gga aag ctc caa tgg gcg tcg     816
Leu Thr Asp Asn Gly Ser Thr Ile Leu Gly Lys Leu Gln Trp Ala Ser
            260                 265                 270 gtc tca gcc ctt ttc tcc tcc atc tct tca cta ctg ccc tcg gat ccg     864
Val Ser Ala Leu Phe Ser Ser Ile Ser Ser Leu Leu Pro Ser Asp Pro
        275                 280                 285
```

```
aaa tct ctc gtc gct tta acg ttt gga ctt tca ctt ata tgg atg act    912
Lys Ser Leu Val Ala Leu Thr Phe Gly Leu Ser Leu Ile Trp Met Thr
    290                 295                 300 tcc tcc tct gcc acc caa acg ctc gtc acc tta acg caa tta gcc acg    960
Ser Ser Ser Ala Thr Gln Thr Leu Val Thr Leu Thr Gln Leu Ala Thr
305                 310                 315                 320 ctg tct gct ctt ttt tac aag agt                                    984
Leu Ser Ala Leu Phe Tyr Lys Ser
                325
```

<210> SEQ ID NO 7
<211> LENGTH: 328
<212> TYPE: PRT
<213> ORGANISM: duck

<400> SEQUENCE: 7

```
Met Gly Gln His Pro Ala Lys Ser Met Asp Val Arg Arg Ile Glu Gly
1               5                   10                  15

Gly Glu Ile Leu Leu Asn Gln Leu Ala Gly Arg Met Ile Pro Lys Gly
            20                  25                  30

Thr Leu Thr Trp Ser Gly Lys Phe Pro Thr Leu Asp His Val Leu Asp
        35                  40                  45

His Val Gln Thr Met Glu Glu Ile Asn Thr Leu Gln Asn Gln Gly Ala
    50                  55                  60

Trp Pro Ala Gly Ala Gly Arg Arg Val Gly Leu Ser Asn Pro Thr Pro
65                  70                  75                  80

Gln Glu Ile Pro Gln Pro Gln Trp Thr Pro Glu Glu Asp Gln Lys Ala
                85                  90                  95

Arg Glu Ala Phe Arg Arg Tyr Gln Glu Glu Arg Pro Pro Glu Thr Thr
            100                 105                 110

Thr Ile Pro Pro Ser Ser Pro Pro Gln Trp Lys Leu Gln Pro Gly Asp
        115                 120                 125

Asp Pro Leu Leu Gly Asn Gln Ser Leu Leu Glu Thr His Pro Leu Tyr
    130                 135                 140

Gln Ser Glu Pro Ala Val Pro Val Ile Lys Thr Pro Pro Leu Lys Lys
145                 150                 155                 160

Lys Met Ser Gly Thr Phe Gly Gly Ile Leu Ala Gly Leu Ile Gly Leu
                165                 170                 175

Leu Val Ser Phe Phe Leu Leu Ile Lys Ile Leu Glu Ile Leu Arg Arg
            180                 185                 190

Leu Asp Trp Trp Trp Ile Ser Leu Ser Ser Pro Lys Gly Lys Met Gln
        195                 200                 205

Cys Ala Phe Gln Asp Thr Gly Ala Gln Ile Ser Pro His Tyr Val Gly
    210                 215                 220

Ser Cys Pro Trp Gly Cys Pro Gly Phe Leu Trp Thr Tyr Leu Arg Leu
225                 230                 235                 240

Phe Ile Ile Phe Leu Leu Ile Leu Leu Val Ala Ala Gly Leu Leu Tyr
                245                 250                 255

Leu Thr Asp Asn Gly Ser Thr Ile Leu Gly Lys Leu Gln Trp Ala Ser
            260                 265                 270

Val Ser Ala Leu Phe Ser Ser Ile Ser Ser Leu Leu Pro Ser Asp Pro
        275                 280                 285

Lys Ser Leu Val Ala Leu Thr Phe Gly Leu Ser Leu Ile Trp Met Thr
    290                 295                 300

Ser Ser Ser Ala Thr Gln Thr Leu Val Thr Leu Thr Gln Leu Ala Thr
305                 310                 315                 320
```

```
Leu Ser Ala Leu Phe Tyr Lys Ser
                325

<210> SEQ ID NO 8
<211> LENGTH: 501
<212> TYPE: DNA
<213> ORGANISM: duck
<220> FEATURE:
<221> NAME/KEY: CDS
<222> LOCATION: (1)..(501)

<400> SEQUENCE: 8 atg tct ggt acc ttc ggg gga ata cta gct ggc cta atc gga tta ctg      48
Met Ser Gly Thr Phe Gly Gly Ile Leu Ala Gly Leu Ile Gly Leu Leu
1               5                   10                  15 gta agc ttt ttc ttg ttg ata aaa att cta gaa ata ctg agg agg cta      96
Val Ser Phe Phe Leu Leu Ile Lys Ile Leu Glu Ile Leu Arg Arg Leu
                20                  25                  30 gat tgg tgg tgg att tct ctc agt tct cca aag gga aaa atg caa tgc     144
Asp Trp Trp Trp Ile Ser Leu Ser Ser Pro Lys Gly Lys Met Gln Cys
            35                  40                  45 gct ttc caa gat act gga gcc caa atc tct cca cat tac gta gga tct     192
Ala Phe Gln Asp Thr Gly Ala Gln Ile Ser Pro His Tyr Val Gly Ser
        50                  55                  60 tgc ccg tgg gga tgc cca gga ttt ctt tgg acc tat ctc agg ctt ttt     240
Cys Pro Trp Gly Cys Pro Gly Phe Leu Trp Thr Tyr Leu Arg Leu Phe
65                  70                  75                  80 atc atc ttc ctc tta atc ctg cta gta gca gca ggc ttg ctg tat ctg     288
Ile Ile Phe Leu Leu Ile Leu Leu Val Ala Ala Gly Leu Leu Tyr Leu
                85                  90                  95 acg gac aac ggg tct act att tta gga aag ctc caa tgg gcg tcg gtc     336
Thr Asp Asn Gly Ser Thr Ile Leu Gly Lys Leu Gln Trp Ala Ser Val
                100                 105                 110 tca gcc ctt ttc tcc tcc atc tct tca cta ctg ccc tcg gat ccg aaa     384
Ser Ala Leu Phe Ser Ser Ile Ser Ser Leu Leu Pro Ser Asp Pro Lys
            115                 120                 125 tct ctc gtc gct tta acg ttt gga ctt tca ctt ata tgg atg act tcc     432
Ser Leu Val Ala Leu Thr Phe Gly Leu Ser Leu Ile Trp Met Thr Ser
        130                 135                 140 tcc tct gcc acc caa acg ctc gtc acc tta acg caa tta gcc acg ctg     480
Ser Ser Ala Thr Gln Thr Leu Val Thr Leu Thr Gln Leu Ala Thr Leu
145                 150                 155                 160 tct gct ctt ttt tac aag agt                                         501
Ser Ala Leu Phe Tyr Lys Ser
                165

<210> SEQ ID NO 9
<211> LENGTH: 167
<212> TYPE: PRT
<213> ORGANISM: duck

<400> SEQUENCE: 9

Met Ser Gly Thr Phe Gly Gly Ile Leu Ala Gly Leu Ile Gly Leu Leu
1               5                   10                  15

Val Ser Phe Phe Leu Leu Ile Lys Ile Leu Glu Ile Leu Arg Arg Leu
                20                  25                  30

Asp Trp Trp Trp Ile Ser Leu Ser Ser Pro Lys Gly Lys Met Gln Cys
            35                  40                  45

Ala Phe Gln Asp Thr Gly Ala Gln Ile Ser Pro His Tyr Val Gly Ser
        50                  55                  60
```

```
Cys Pro Trp Gly Cys Pro Gly Phe Leu Trp Thr Tyr Leu Arg Leu Phe
 65              70                  75                  80

Ile Ile Phe Leu Leu Ile Leu Val Ala Ala Gly Leu Leu Tyr Leu
                 85                  90                  95

Thr Asp Asn Gly Ser Thr Ile Leu Gly Lys Leu Gln Trp Ala Ser Val
            100                 105                 110

Ser Ala Leu Phe Ser Ser Ile Ser Ser Leu Leu Pro Ser Asp Pro Lys
            115                 120                 125

Ser Leu Val Ala Leu Thr Phe Gly Leu Ser Leu Ile Trp Met Thr Ser
        130                 135                 140

Ser Ser Ala Thr Gln Thr Leu Val Thr Leu Thr Gln Leu Ala Thr Leu
145             150                 155                 160

Ser Ala Leu Phe Tyr Lys Ser
                165

<210> SEQ ID NO 10
<211> LENGTH: 483
<212> TYPE: DNA
<213> ORGANISM: duck
<220> FEATURE:
<221> NAME/KEY: CDS
<222> LOCATION: (1)..(483)

<400> SEQUENCE: 10 atg ggg caa cat cca gca aaa tca atg gac gtc aga cgg ata gaa gga    48
Met Gly Gln His Pro Ala Lys Ser Met Asp Val Arg Arg Ile Glu Gly
  1               5                  10                  15 gga gaa ata ctg tta aac caa ctt gcc gga agg atg atc cca aaa ggg    96
Gly Glu Ile Leu Leu Asn Gln Leu Ala Gly Arg Met Ile Pro Lys Gly
                 20                  25                  30 act ttg aca tgg tca ggc aag ttt cca aca cta gat cac gtg tta gac   144
Thr Leu Thr Trp Ser Gly Lys Phe Pro Thr Leu Asp His Val Leu Asp
             35                  40                  45 cat gtg caa aca atg gag gag ata aac acc ctc cag aat cag gga gct   192
His Val Gln Thr Met Glu Glu Ile Asn Thr Leu Gln Asn Gln Gly Ala
         50                  55                  60 tgg cct gct ggg gcg gga agg aga gta gga tta tca aat ccg act cct   240
Trp Pro Ala Gly Ala Gly Arg Arg Val Gly Leu Ser Asn Pro Thr Pro
 65              70                  75                  80 caa gag att cct cag ccc cag tgg act ccc gag gaa gac caa aaa gca   288
Gln Glu Ile Pro Gln Pro Gln Trp Thr Pro Glu Glu Asp Gln Lys Ala
                 85                  90                  95 cgc gaa gct ttt cgc cgt tat caa gaa gaa aga cca ccg gaa acc acc   336
Arg Glu Ala Phe Arg Arg Tyr Gln Glu Glu Arg Pro Pro Glu Thr Thr
            100                 105                 110 acc att cct ccg tct tcc cct cct cag tgg aag cta caa ccc ggg gac   384
Thr Ile Pro Pro Ser Ser Pro Pro Gln Trp Lys Leu Gln Pro Gly Asp
        115                 120                 125 gat cca ctc ctg gga aat cag tct ctc ctc gag act cat ccg cta tac   432
Asp Pro Leu Leu Gly Asn Gln Ser Leu Leu Glu Thr His Pro Leu Tyr
    130                 135                 140 cag tca gaa cca gcg gtg cca gtg ata aaa act ccc ccc ttg aag aag   480
Gln Ser Glu Pro Ala Val Pro Val Ile Lys Thr Pro Pro Leu Lys Lys
145                 150                 155                 160 aaa                                                                483
Lys

<210> SEQ ID NO 11
<211> LENGTH: 161
<212> TYPE: PRT
```

<213> ORGANISM: duck

<400> SEQUENCE: 11

```
Met Gly Gln His Pro Ala Lys Ser Met Asp Val Arg Arg Ile Glu Gly
1               5                   10                  15

Gly Glu Ile Leu Leu Asn Gln Leu Ala Gly Arg Met Ile Pro Lys Gly
                20                  25                  30

Thr Leu Thr Trp Ser Gly Lys Phe Pro Thr Leu Asp His Val Leu Asp
            35                  40                  45

His Val Gln Thr Met Glu Glu Ile Asn Thr Leu Gln Asn Gln Gly Ala
        50                  55                  60

Trp Pro Ala Gly Ala Gly Arg Arg Val Gly Leu Ser Asn Pro Thr Pro
65                  70                  75                  80

Gln Glu Ile Pro Gln Pro Gln Trp Thr Pro Glu Glu Asp Gln Lys Ala
                85                  90                  95

Arg Glu Ala Phe Arg Arg Tyr Gln Glu Glu Arg Pro Pro Glu Thr Thr
            100                 105                 110

Thr Ile Pro Pro Ser Ser Pro Pro Gln Trp Lys Leu Gln Pro Gly Asp
        115                 120                 125

Asp Pro Leu Leu Gly Asn Gln Ser Leu Leu Glu Thr His Pro Leu Tyr
    130                 135                 140

Gln Ser Glu Pro Ala Val Pro Val Ile Lys Thr Pro Pro Leu Lys Lys
145                 150                 155                 160

Lys
```

<210> SEQ ID NO 12
<211> LENGTH: 501
<212> TYPE: DNA
<213> ORGANISM: duck
<220> FEATURE:
<221> NAME/KEY: CDS
<222> LOCATION: (1)..(501)

<400> SEQUENCE: 12

```
atg tct ggt acc ttc ggg gga ata cta gct ggc cta atc gga tta ctg    48
Met Ser Gly Thr Phe Gly Gly Ile Leu Ala Gly Leu Ile Gly Leu Leu
1               5                   10                  15 gta agc ttt ttc ttg ttg ata aaa att cta gaa ata ctg agg agg cta    96
Val Ser Phe Phe Leu Leu Ile Lys Ile Leu Glu Ile Leu Arg Arg Leu
                20                  25                  30 gat tgg tgg tgg att tct ctc agt tct cca aag gga aaa atg caa tgc    144
Asp Trp Trp Trp Ile Ser Leu Ser Ser Pro Lys Gly Lys Met Gln Cys
            35                  40                  45 gct ttc caa gat act gga gcc caa atc tct cca cat tac gta gga tct    192
Ala Phe Gln Asp Thr Gly Ala Gln Ile Ser Pro His Tyr Val Gly Ser
        50                  55                  60 tgc ccg tgg gga tgc cca gga ttt ctt tgg acc tat ctc agg ctt ttt    240
Cys Pro Trp Gly Cys Pro Gly Phe Leu Trp Thr Tyr Leu Arg Leu Phe
65                  70                  75                  80 atc atc ttc ctc tta atc ctg cta gta gca gca ggt tgc ctg tat ctg    288
Ile Ile Phe Leu Leu Ile Leu Leu Val Ala Ala Gly Leu Leu Tyr Leu
                85                  90                  95 acg gac aac ggg tct act att tta gga aag ctc caa tgg gcg tcg gtc    336
Thr Asp Asn Gly Ser Thr Ile Leu Gly Lys Leu Gln Trp Ala Ser Val
            100                 105                 110 tca gcc ctt ttc tcc tcc atc tct tca cta ctg ccc tcg gat ccg aaa    384
Ser Ala Leu Phe Ser Ser Ile Ser Ser Leu Leu Pro Ser Asp Pro Lys
        115                 120                 125
```

-continued

```
tct ctc gtc gct tta acg ttt gga ctt tca ctt ata tgg atg act tcc      432
Ser Leu Val Ala Leu Thr Phe Gly Leu Ser Leu Ile Trp Met Thr Ser
    130                 135                 140 tcc tct gcc acc caa acg ctc gtc acc tta acg caa tta gcc acg ctg      480
Ser Ser Ala Thr Gln Thr Leu Val Thr Leu Thr Gln Leu Ala Thr Leu
145                 150                 155                 160 tct gct ctt ttt tac aag agt                                          501
Ser Ala Leu Phe Tyr Lys Ser
                165

<210> SEQ ID NO 13
<211> LENGTH: 167
<212> TYPE: PRT
<213> ORGANISM: duck

<400> SEQUENCE: 13

Met Ser Gly Thr Phe Gly Gly Ile Leu Ala Gly Leu Ile Gly Leu Leu
1               5                   10                  15

Val Ser Phe Phe Leu Leu Ile Lys Ile Leu Glu Ile Leu Arg Arg Leu
            20                  25                  30

Asp Trp Trp Trp Ile Ser Leu Ser Ser Pro Lys Gly Lys Met Gln Cys
        35                  40                  45

Ala Phe Gln Asp Thr Gly Ala Gln Ile Ser Pro His Tyr Val Gly Ser
    50                  55                  60

Cys Pro Trp Gly Cys Pro Gly Phe Leu Trp Thr Tyr Leu Arg Leu Phe
65                  70                  75                  80

Ile Ile Phe Leu Leu Ile Leu Leu Val Ala Ala Gly Leu Leu Tyr Leu
                85                  90                  95

Thr Asp Asn Gly Ser Thr Ile Leu Gly Lys Leu Gln Trp Ala Ser Val
            100                 105                 110

Ser Ala Leu Phe Ser Ser Ile Ser Ser Leu Leu Pro Ser Asp Pro Lys
        115                 120                 125

Ser Leu Val Ala Leu Thr Phe Gly Leu Ser Leu Ile Trp Met Thr Ser
    130                 135                 140

Ser Ser Ala Thr Gln Thr Leu Val Thr Leu Thr Gln Leu Ala Thr Leu
145                 150                 155                 160

Ser Ala Leu Phe Tyr Lys Ser
                165
```